US012245999B2

(12) United States Patent
Jern et al.

(10) Patent No.: US 12,245,999 B2
(45) Date of Patent: *Mar. 11, 2025

(54) VALPROIC ACID FOR THE TREATMENT OR PREVENTION OF PATHOLOGICAL CONDITIONS ASSOCIATED WITH EXCESS FIBRIN DEPOSITION AND/OR THROMBUS FORMATION

(71) Applicant: Cereno Scientific AB, Gothenburg (SE)

(72) Inventors: Sverker Jern, Ljungskile (SE); Jonas Faijerson Saljo, Gothenburg (SE); Niklas Bergh, Askim (SE)

(73) Assignee: Cereno Scientific AB, Gothenburg (SE)

( * ) Notice: Subject to any disclaimer, the term of this patent is extended or adjusted under 35 U.S.C. 154(b) by 327 days.

This patent is subject to a terminal disclaimer.

(21) Appl. No.: 17/816,486

(22) Filed: Aug. 1, 2022

(65) Prior Publication Data

US 2022/0401393 A1 Dec. 22, 2022

Related U.S. Application Data

(60) Continuation of application No. 16/135,639, filed on Sep. 19, 2018, now Pat. No. 11,400,064, which is a division of application No. 15/517,229, filed as application No. PCT/GB2015/052950 on Oct. 8, 2015, now Pat. No. 10,111,845.

(30) Foreign Application Priority Data

Aug. 10, 2014 (GB) ...................................... 1417828

(51) Int. Cl.
| | | |
|---|---|---|
| A61K 31/19 | (2006.01) | |
| A61K 9/28 | (2006.01) | |
| A61K 9/48 | (2006.01) | |
| A61K 31/4365 | (2006.01) | |
| A61K 31/519 | (2006.01) | |
| A61K 31/616 | (2006.01) | |

(52) U.S. Cl.
CPC ................ *A61K 31/19* (2013.01); *A61K 9/28* (2013.01); *A61K 9/4891* (2013.01); *A61K 31/4365* (2013.01); *A61K 31/519* (2013.01); *A61K 31/616* (2013.01)

(58) Field of Classification Search
CPC ............................. A61K 31/19; A61K 31/616
See application file for complete search history.

(56) References Cited

U.S. PATENT DOCUMENTS

| | | |
|---|---|---|
| 5,049,586 A | 9/1991 | Ortega et al. |
| 2004/0043026 A1 | 3/2004 | Tuan et al. |
| 2004/0170684 A1 | 9/2004 | Baichwal et al. |
| 2004/0224006 A1 | 11/2004 | Raffaniello |
| 2005/0276848 A1 | 12/2005 | Podhipleux et al. |
| 2005/0276850 A1 | 12/2005 | Podhipleux et al. |
| 2006/0178437 A1 | 8/2006 | Kammer et al. |
| 2009/0048156 A1 | 2/2009 | Brodie et al. |
| 2009/0048300 A1 | 2/2009 | Chen et al. |
| 2009/0088410 A1 | 4/2009 | Zeldis |
| 2009/0270497 A1 | 10/2009 | Buggy |
| 2013/0022676 A1 | 1/2013 | Mullen et al. |
| 2014/0051716 A1 | 2/2014 | Larsson et al. |
| 2014/0341989 A1 | 11/2014 | Loury et al. |
| 2017/0020874 A1 | 1/2017 | Larsson et al. |
| 2018/0177751 A1 | 6/2018 | Jern et al. |
| 2019/0111011 A1 | 4/2019 | Gustafsson et al. |
| 2020/0179381 A1 | 6/2020 | Bergh et al. |
| 2023/0094176 A1 | 3/2023 | Larsson et al. |
| 2023/0120670 A1 | 4/2023 | Gustafsson et al. |

FOREIGN PATENT DOCUMENTS

| | | |
|---|---|---|
| CN | 101947209 B | 7/2012 |
| EP | 1743654 A1 | 1/2007 |
| EP | 1815850 B1 | 11/2008 |
| IN | 236664 B | 11/2009 |
| WO | 2001039747 | 6/2001 |
| WO | 2002055017 | 7/2002 |
| WO | 2003013493 | 2/2003 |
| WO | 2005105066 A2 | 11/2005 |
| WO | 2006117165 A2 | 11/2006 |
| WO | 2007030697 A2 | 3/2007 |
| WO | 2007084775 A2 | 7/2007 |
| WO | 2007115287 A2 | 10/2007 |
| WO | 2008027993 A2 | 3/2008 |
| WO | 2011107749 A2 | 9/2011 |
| WO | 2011113013 A2 | 9/2011 |
| WO | 2012120262 A1 | 9/2012 |
| WO | 2016055797 A2 | 4/2016 |

OTHER PUBLICATIONS

"U.S. Appl. No. 17/746,537; office action mailed Aug. 30, 2023".
Atmaca, A , et al., "Valproic acid (VPA) in patients with refractory advanced cancer: a dose escalating phase I clinical trial", British Journal of Cancer 97:177-182 (Jun. 19, 2007).
Banerjea, M. C, et al., "Pro- and anticoagulatory factors under sodium valproate-therapy in children", Neuropediatrics 33(4):215-220 (2002).
Cesari, Matteo , et al., "Plasminogen Activator Inhibitor-1 (PAI-1): a Key Factor Linking Fibrinolysis and Age-Related Subclinical and Clinical Conditions", Cardiovasc Ther 28(5):e72-e91 (Oct. 2010).
Qi, Xiaolian , et al., "Analysis of 15 cases of hypofibrinogenemia induced by sodium valproate", Yaowu Liuxingbingxue Zazhi 19(4):206-208 (2010).

(Continued)

*Primary Examiner* — Genevieve S Alley
(74) *Attorney, Agent, or Firm* — Myers Bigel, P.A.

(57) ABSTRACT

There is herein provided valproic acid, or a pharmaceutically acceptable salt thereof, for use in treating or preventing a pathological condition associated with excess fibrin deposition and/or thrombus formation, wherein said treatment comprises treating a patient with valproic acid, or a pharmaceutically acceptable salt thereof, in a specific manner, and formulations for use or designed for use in such treatments.

17 Claims, 1 Drawing Sheet

(56) References Cited

OTHER PUBLICATIONS

"U.S. Appl. No. 17/868,323; office action mailed Oct. 3, 2023".
"U.S. Appl. No. 17/746,537; office action mailed Jun. 4, 2024".
Nakstad, B , et al., "Immunohistochemical localization of coagulation, fibrinolytic and antifibrinolytic markers in adenocarcinoma of the lung", APMIS 99(11):981-8 (Nov. 1991).
"U.S. Appl. No. 14/955,922; Office Action mailed Oct. 16, 2019".
"U.S. Appl. No. 16/090,661; Office Action mailed Mar. 21, 2022".
"U.S. Appl. No. 16/090,661; Office Action mailed Sep. 1, 2021".
"U.S. Appl. No. 16/090,664; Office Action mailed Aug. 16, 2021".
"U.S. Appl. No. 16/090,664; Office Action mailed Aug. 8, 2019".
"U.S. Appl. No. 16/090,664; Office Action mailed Feb. 25, 2020".
"U.S. Appl. No. 16/135,639; Office Action mailed Feb. 4, 2021".
"U.S. Appl. No. 16/135,639; Office Action mailed Jul. 31, 2020".
"U.S. Appl. No. 16/135,639; Office Action mailed Oct. 30, 2019".
"U.S. Appl. No. 16/135,639; Office Action mailed Sep. 15, 2021".
"U.S. Appl. No. 17/477,248; Office Action mailed Jan. 21, 2022".
"Diaz "Inflammation and Acute Venous Thrombosis" US Oncology & Hematology, 7(1):68-71 (2011)".
"FDA (https://www.accessdata.fda.gov/drugsatfda docs/label/20 11/018081 s0461 8082s03 1 lbl .pdf, 2011). (Year: 2011)".
"Final Office Action corresponding to U.S. Appl. No. 14/955,922, dated Feb. 2, 2018, 13 pages".
"Final Office Action Corresponding to U.S. Appl. No. 14/003,780; Mail Date: Jul. 1, 2015; 16 pages".
"Guidance for Industry: Estimating the Maximum Safe Starting Dose in Initial Clinical Trials for Therapeutics in Adult Healthy Volunteers, Pharmacology and Toxicology (2005) 30 pages".
"http://medical-dictionary.thefreedictionary.com/prevention accessed on Nov. 21, 2014".
"International Search Report and Written Opinion corresponding to International Application No. PCT/GB2012/000229, mailed May 18, 2012 (11 pages)".
"International Search Report and Written Opinion Corresponding to International Application No. PCT/GB2015/052950; Date of Mailing: Apr. 19, 2016; 23 Pages".
"International Search Report and Written Opinion corresponding to International Application No. PCT/GB2017/051002, mailed Jul. 13, 2017, 16 pages."
"International Search Report and Written Opinion corresponding to International Patent Application No. PCT/GB2017/050997, mailed Sep. 22, 2017, 19 pages".
"International Search Report and Written Opinion corresponding to International Patent Application No. PCT/GB2017/051002, mailed Jul. 13, 2017, 16 pages".
"Non Final Office Action Corresponding to U.S. Appl. No. 14/003,780; Mail Date: Nov. 25, 2014, 16 pages".
"Non-Final Office Action Corresponding to U.S. Appl. No. 14/955,922; Mail Date: Apr. 27, 2017; 13 pages".
"Non-Final Office Action Corresponding to U.S. Appl. No. 14/955,922; Mail Date: Jan. 7, 2019; 10 pages".
"Valproic Acid", NHS reviewed: Sep. 24, 2018. (Year: 2018).
"WebMD, "How to Prevent Deep Vein Thrombosis (DVT)", http://www.webmd.com/dvt/deep-vein-thrombosis-prevent-dvt#1 accessed on Apr. 24, 2017".
Angleton , et al., ""Diurnal variation of tissue-type plasminogen activator and its rapid inhibitor (PAI-1)" Circulation, 79(1):101-106 (1989)".
Angleton , et al., ", "Diurnal variation of tissue-type plasminogen activator and its rapid inhibitor (PAI-1)", Circulation, US, (1989), 79(1):101-106".
Bruce , et al., ""Properties of Enteric Coated Sodium Valproate Pellets", International Journal of Pharmaceutics, Elsevier, 264(1/02):85-96 (2003) Abstract".
Cho , et al., ""Valproic Acid Induces Astrocyte-Dependent Neurite Outgrowth from Cultured Rat Primary Cortical Neuron Via Modulation of tPA/PAI-1 Activity", Feb. 4, 2013, Wiley Online Library, 694-709".
Christiansen , et al., ""Inflammatory Cytokines as Risk Factors for a First Venous Thrombosis: A Prospective Population-Based Study" PLoS Medicine, 3(8):1414-1419 (2006)".
Collen , et al., ""Tissue-type plasminogen activator: a historical perspective and personal account" Journal of Thrombosis and Haemostasis, (2004) pp. 541-546".
Cugno , et al., ""Antibodies to tissue-type plasminogen activator in plasma from patients with primary antiphospholipid syndrome" British Journal of Haematology, 108:871-875 (2000)".
Falanga , et al., ""Deep vein thrombosis in cancer: the scale of the problem and approaches to management" Annals of Oncology, 16:696-701, 2005".
Furlan, Antonio , et al., "Pharmacokinetics, Safety and Inducible Cytokine Responses during a Phase 1 Trial of the Oral Histone Deacetylase Inhibitor ITF2357 (Givinostat)", Mol Med 17(5-6):353-362 (May-Jun. 2011).
Galli , et al., ""A phase II multiple dose clinical trial of histone deacetylase inhibitor ITF2357 in patients with relapsed or progressive multiple myeloma" Ann. Hematol (2010), 89:185-190".
Goldenberg , et al., ""Markers of Coagulation and Angiogenesis in Cancer-Associated Venous Thromboembolism", Journal of Clinical Oncology, vol. 21, No. 22, Nov. 15, 2003, pp. 4194-4199".
Larsson , et al., "Poster Entitled, "Valproic Acid Stimulates t-PA Expression in Human Endothelial Cells," Epigenetics, 2009 Australian Scientific Conference, Melbourne, Australia, Dec. 1-4, 2009".
Leoni , et al., ""The Histone Deacetylase Inhibitor ITF2357 Reduces Production of Pro-Inflammatory Cytokines In Vitro and Systemic Inflammation in Vivo", Molecular Medicine, 11:1-15 (2005)".
Novotny-Diermayr , et al., ""SB939, a Novel Potent and Orally Active Histone Deacetylase Inhibitor with High Tumor Exposure and Efficacy in Mouse Models of Colorectal Cancer", Mol. Cancer Ther; 9(3):642-652, Mar. 9, 2010".
Ojemann , et al., ", "Fibrinogen and Valproic-Acid," Epilepsia, 22(2):242-243 1981".
Rambaldi , et al., ""A pilot study of the Histone-Deacetylase inhibitor Givinostat in patients with JAK2V617F positive chronic myeloproliferative neoplasms" British Journal of Haemotology, 150:446-455 (2010)".
Ren , et al., ""Valproic acid reduces brain damage induced by transient focal cerebral ischemia in rats: potential roles of histone deacetylase inhibition and heat shock protein induction" Journal of Neurochemistry, 2004, 89:1358-1367".
Saluveer , et al., ""Profibrinolytic Effect of the Epigenetic Modifier Valproic Acid in Man" PLOS ONE, (2014), 9(10) 7 pages".
Saluveer , et al., ", "Profibrinolytic Effect of the Epigenetic Modifier Valproic Acid in Man", PLOS ONE, (Oct. 2014), vol. 9, No. 10; 7 pages".
Scheer, Frank A.J.L, et al., "Human circadian system causes a morning peak in prothrombotic plasminogen activator inhibitor-1 (PAI-1) independent of the sleep/wake cycle", Blood 123(4):590-593 (Jan. 23, 2014).
Steinbrugger , et al., ""Analysis of inflammation- and atherosclerosis-related gene polymorphisms in branch retinal vein occlusion", Mol Vis., 15:609-618 (2009)".
Sutor , et al., ", "Influence of dipropylacetic acid (Ergenyl) on blood clotting," Medizinische Welt, vol. 25, No. 11, 1974, pp. 447-449 English translation".
Svennerholm , et al., ", "Histone Deacetylase Inhibition Enhances Tissue Plasminogen Activator Release Capacity in Atherosclerotic Man" PLOS ONE, (Mar. 2015), vol. 10, No. 3; 13 pages".
Tabrizi , et al., ""Tissue Plasminogen Activator (IPA) Deficiency Exacerbates Cerebrovascular Fibrin Deposition and Brain Injury in a Murine Stroke Model: Studies in tPA-Deficient Mice and Wild-Type Mice on a Matched Genetic Background" Arterioscler Thromb Vasc Biol., 1999,".
Tsunaka , et al., ""Cell-based laboratory evaluation of coagulation activation by antineoplastic drugs for the treatment of lymphoid tumors", SAGE Open Med., vol. 4: 1-9, 2016".
Wang , et al., ""Beneficial effects of mood stabilizers lithium, valproate and lamotrigine in experimental stroke models", Review. Acta Pharmacologica Sinica, (2011) 32: 1433-1445".

(56) References Cited

OTHER PUBLICATIONS

Wang, et al., ""Histone Deacetylase Inhibitors Suppress TF-KB-dependent Agonist-driven Tissue Factor Expression in Endothelial Cells and Monocytes", The Journal of Biological Chemistry, 282:28408-28418 (2007)".

Woyach, et al., ""Lack of Therapeutic Effect of the Histone Deacetylase Inhibitor Vorinostat in Patients with Metastatic Radioiodine-Refractory Thyroid Carcinoma" J Clin Endocrinol Metab., 94(1):164-170 2009".

Yong, et al., "A phase I dose escalation study of oral SB939 when administered thrice weekly (every other day) for 3 weeks in a 4-week cycle in patients with advanced solid malignancies. Eur J Cancer, 6 (2008) abstract".

Zeller, et al., ""Influence of Valproate Monotherapy on Platelet Activation and Hematologic Values" Epilepsia 40 (2):186-189 (1999)".

"U.S. Appl. No. 17/838,323; office action mailed Jul. 3, 2023".

"U.S. Appl. No. 16/090,661; Office Action mailed Jan. 27, 2023".

"U.S. Appl. No. 18/360,200; office action mailed Jan. 14, 2025",.

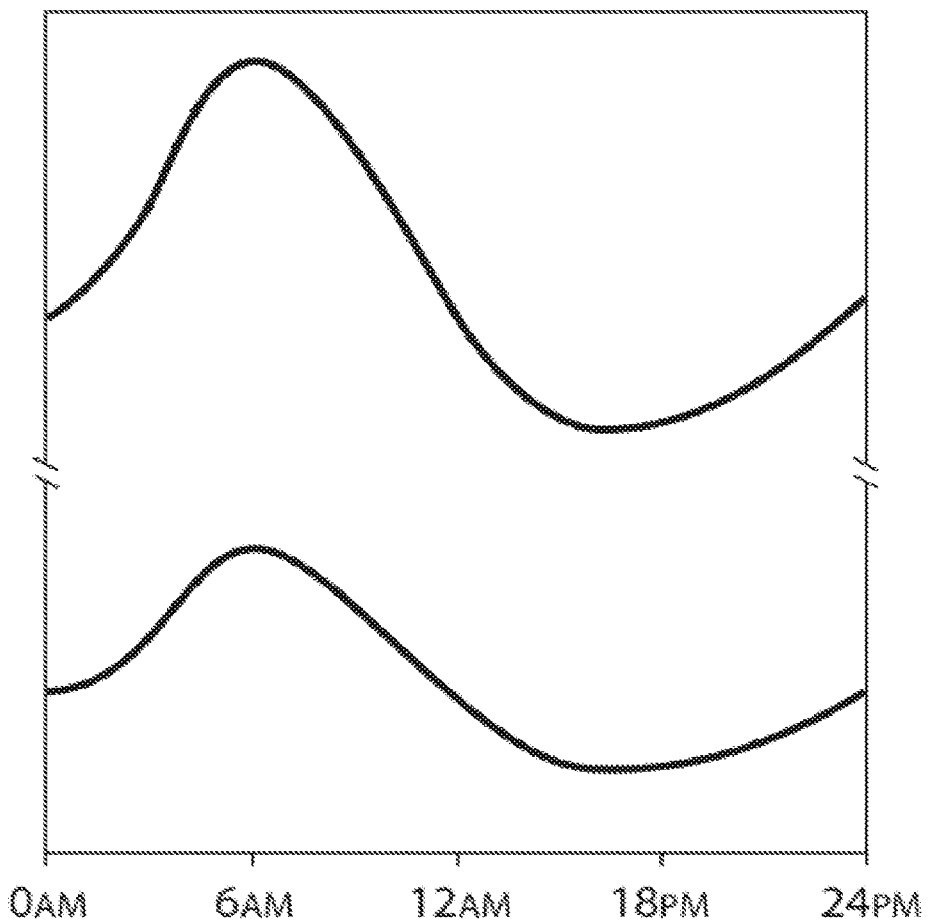

VALPROIC ACID FOR THE TREATMENT OR PREVENTION OF PATHOLOGICAL CONDITIONS ASSOCIATED WITH EXCESS FIBRIN DEPOSITION AND/OR THROMBUS FORMATION

STATEMENT OF PRIORITY

This application is a continuation application of U.S. patent application Ser. No. 16/135,639, filed on Sep. 19, 2018, now U.S. Pat. No. 11,400,064, which is a divisional application of U.S. patent application Ser. No. 15/517,229; filed on Apr. 6, 2017, now U.S. Pat. No. 10,111,845, which is a 35 U.S.C. § 371 national phase application of International Application Serial No. PCT/GB2015/052950, filed on Oct. 8, 2015, which claims the benefit, under 35 U.S.C. § 119(a) of United Kingdom Patent Application No. 1417828.9, filed on Oct. 8, 2014, the entire content of each of which are incorporated herein by reference.

FIELD OF THE INVENTION

The present invention generally relates to new medical uses, methods of treatment and pharmaceutical compositions. More specifically, it relates to the use of valproic acid (VPA), and pharmaceutically acceptable salts thereof, in the treatment or prevention of thrombus formation and in improving or normalizing endogenous vascular fibrinolysis.

BACKGROUND OF THE INVENTION

The listing or discussion of an apparently prior-published document in this specification should not necessarily be taken as an acknowledgement that the document is part of the state of the art or is common general knowledge.

Cardiovascular disease is the leading cause of morbidity and mortality in the western world and during the last decades it has also become a rapidly increasing problem in developing countries. An estimated 80 million American adults (one in three) have one or more expressions of cardiovascular disease (CVD), such as hypertension, coronary heart disease, heart failure, or stroke. Mortality data show that CVD was the underlying cause of death in 35% of all deaths in 2005 in the United States, with the majority related to myocardial infarction, stroke, or complications thereof. The vast majority of patients suffering acute cardiovascular events have prior exposure to at least one major risk factor, such as cigarette smoking, abnormal blood lipid levels, hypertension, diabetes, abdominal obesity and low-grade inflammation.

Pathophysiologically, the major events of myocardial infarction and ischemic stroke are caused by a sudden arrest of nutritive blood supply due to a blood clot formation within the lumen of the arterial blood vessel. In most cases, formation of the thrombus is precipitated by rupture of a vulnerable atherosclerotic plaque, which exposes chemical agents that activate platelets and the plasma coagulation system. The activated platelets form a platelet plug that is armed by coagulation-generated fibrin to form a blood clot that expands within the vessel lumen until it obstructs or blocks blood flow, which results in hypoxic tissue damage (so-called infarction). Thus, thrombotic cardiovascular events occur as a result of two distinct processes, i.e. a slowly progressing long-term vascular atherosclerosis of the vessel wall, on the one hand, and a sudden acute clot formation that rapidly causes flow arrest, on the other. Without wishing to be bound by theory, it is thought that the present invention solely relates to the latter process.

Recently, inflammation has been recognized as an important risk factor for thrombotic events. Vascular inflammation is a characteristic feature of the atherosclerotic vessel wall, and inflammatory activity is a strong determinant of the susceptibility of the atherosclerotic plaque to rupture and initiate intravascular clotting. Also, autoimmune conditions with systemic inflammation, such as rheumatoid arthritis, systemic lupus erythematosus and different forms of vasculitides, markedly increase the risk of myocardial infarction and stroke.

Traditional approaches to prevent and treat cardiovascular events are targeted: 1) to slow down the progression of the underlying atherosclerotic process; 2) to prevent clot formation in case of a plaque rupture; or 3) to direct removal of an acute thrombotic flow obstruction. In short, antiatherosclerotic treatment aims at modulating the impact of general risk factors and includes dietary recommendations, weight loss, physical exercise, smoking cessation, cholesterol- and blood pressure treatment etc.

Prevention of clot formation mainly relies on the use of antiplatelet drugs that inhibit platelet activation and/or aggregation, but also in some cases includes thromboembolic prevention with oral anticoagulants such as warfarin. Post hoc treatment of acute atherothrombotic events requires either direct pharmacological lysis of the clot by thrombolytic agents such as recombinant tissue-type plasminogen activator or percutaneous mechanical dilation of the obstructed vessel.

Despite the fact that multiple-target anti-atherosclerotic therapy and clot prevention by antiplatelet agents have lowered the incidence of myocardial infarction and ischemic stroke, such events still remain a major population health problem. This shows that in patients with cardiovascular risk factors these prophylactic measures are insufficient to completely prevent the occurrence of atherothrombotic events.

Likewise, thrombotic conditions on the venous side of the circulation, as well as embolic complications thereof such as pulmonary embolism, still cause substantial morbidity and mortality. Venous thrombosis has a different clinical presentation and the relative importance of platelet activation versus plasma coagulation are somewhat different, with a preponderance for the latter in venous thrombosis. However, despite these differences, the major underlying mechanisms that cause thrombotic vessel occlusions are similar to those operating on the arterial circulation. Moreover, although unrelated to atherosclerosis as such, the risk of venous thrombosis is related to general cardiovascular risk factors, such as inflammation and metabolic aberrations.

Taken together, existing therapy and general risk factor management offers insufficient protection against thrombotic events, both in the arterial and venous circulations, and cannot reverse the severe consequences of such events. This creates a need for development of novel preventive and therapeutic targets, especially more effective approaches that could prevent hazardous tissue ischemia, and ideally at such an early stage that symptoms have not yet occurred.

Interestingly, it has been found that, in an otherwise healthy individual, there is a natural "last line of defense" system, which can be activated if a clotting process, despite preventive measures, should occur in the vasculature. In brief, initiation of a thrombotic mechanism both on the arterial and venous sides of the circulation leads to activation of the innermost cell layer of the blood vessel (the endothelium), and as a response the cells rapidly release large amounts of the clot-dissolving substance tissue-type plasminogen activator (t-PA). This raises luminal t-PA levels to similar levels as with clinical thrombolytic therapy (i.e. administration of recombinant t-PA), but the potency of this endogenous response is 100-fold greater due to the extremely rapid onset of action.

Accumulating clinical, epidemiologic, and experimental data support the notion that if this thromboprotective function of the blood vessel wall is intact, it offers a powerful defense against formation of flow-arresting thrombi. Unfortunately, however, the capacity for acute t-PA release is impaired in several conditions with increased susceptibility to thrombotic events. These include atherosclerosis, hypertension, abdominal obesity, smoking, sedentary lifestyle, and low-grade inflammation. This impairment is most likely due to a diminished synthesis and thereby reduced availability of the fibrinolytic activator in the endothelial cells.

In addition, we and others have shown that the efficiency of the endogenous fibrinolytic response is reduced in patients with increased risk for an atherothrombotic event, such as in atherosclerosis (Osterlund, B., et al. *Acta Anaesthesiol Scand* 52, 1375-1384 (2008), Newby, D. E., et al. *Circulation* 103, 1936-1941 (2001)). Recent data suggest that inflammation may be an underlying pathogenetic mechanism behind the suppressed t-PA production in this state. We have shown that prolonged exposure to the inflammatory cytokines tumor necrosis factor alpha (TNF-alpha) and interleukin-1 beta (IL-1b) causes a marked suppression of the transcription of t-PA (Ulfhammer, E., et al. *Journal of Thrombosis and Haemostasis* 4, 1781-1789 (2006), Larsson, P., et al. *Thromb Res* 123, 342-351 (2008)). Interestingly, it is known that the atherosclerotic plaque is associated with a local, potentially severe, inflammatory activation in the vessel wall and it is conceivable that this inflammatory milieu hampers the fibrinolytic response in the specific areas of the vasculature where it is pivotal to retain a high fibrinolytic capacity, thus increasing the risk of thrombotic events. Similarly, it is also likely that the increased incidence of thrombotic events in patients with systemic inflammatory conditions (e.g. autoimmune diseases and the metabolic syndrome), could also be related to a suppressive effect of circulating pro-inflammatory cytokines on t-PA synthesis and/or increased levels of plasminogen activator inhibitor 1 (PAI-1).

Against this background, an alternative fourth approach to reduce the incidence of clinical thrombotic events should be to restore the capacity of the fibrinolytic 'last line of defense' system in patients with an impairment of its function. Extensive efforts have been made to find a feasible means for enhancing basal as well as stimulated endogenous fibrinolysis in subjects with a risk factor-associated reduction of fibrinolytic capacity. However, previous attempts to ameliorate t-PA synthesis with e.g. statins and retinoic acid have been disappointing. Other means of increasing fibrinolysis by blocking naturally occurring inhibitors of t-PA activity such as plasminogen activator inhibitor-1 (PAI-1) and carboxypeptidase U (CPU) have also been unsuccessful mainly due to limited drugability, such as poor pharmacokinetic properties of the drug candidates.

The fibrinolytic activity of t-PA is inhibited by plasminogen activator inhibitor 1 (PAI-1) through complex-binding to the t-PA molecule. By virtue of its antifibrinolytic effect, PAI-1 diminishes the ability to dissolve blood clots and thereby increase the risk of clinical thrombotic events (Hrafnklsdottir et al, J Thromb Haemost 2004; 2:1960-8).

PAI-1 circulates in low concentrations in plasma (typically around 5-10 ng/mL in morning samples), but in the population plasma PAI-1 concentration shows a marked right-wardly skewed distribution. Generally, circulating PAI-1 levels increase with age. Elevated PAI-1 levels predispose for thrombotic events. On an individual scale, levels above 100 ng/mL are considered to constitute a significant risk factor for cardiovascular events, even in the absence of other traditional risk factors. Moreover, elevated PAI-1 levels are frequently found in patients with obesity-related metabolic disorders such as Type-2 diabetes mellitus and the metabolic syndrome.

Circulating levels of PAI-1 show a pronounced circadian variation, with peak levels around 06:00 hours and a trough around 16:00 hours as illustrated in FIG. 1 (see also e.g. Scheer and Shea, Blood 2014). As expected, the morning PAI-1 rise coincides with the temporal peak incidence for thrombotic events, such as myocardial infarction.

Patients with obesity and/or the metabolic syndrome have higher circulating PAI-1 levels and augmented circadian peaks as illustrated in FIG. 1. Plasma concentrations typically range between 15-60 ng/mL in morning samples in these patients, but levels are non-normally distributed with a pronounced positive skewness. Plasma PAI-1 levels between 100-500 mg/mL in morning samples are not infrequently observed in obese patients with the metabolic syndrome. Thus, patients with obesity and/or the metabolic syndrome are at particular risk of suffering thrombotic events resulting from the inhibitory effect of PAI-1 on the action of t-PA.

Therefore, it would be interesting to prevent cardiovascular events by lowering PAI-1, and more specifically to abrogate the early morning rise in its plasma concentration. This approach would theoretically be even more efficient in patients with obesity and/or the metabolic syndrome.

We have now surprisingly found that valproic acid (VPA) potently reduces plasma PAI-1 levels, with such reduction, and corresponding reduction in PAI-1 activity, allowing for an increase in the activity of endogenous t-PA. Thus, administration of VPA in low doses in a manner such that plasma levels of VPA, or metabolites thereof, coincide with peak plasma levels of PAI-1 allows for an advantageous effect in the treatment or prevention of pathological conditions associated with excess fibrin deposition and/or thrombus formation.

WO 2012/120262 discusses the use of valproic acid in improving or normalizing endogenous fibrinolysis impaired by local or systemic inflammation. However, it provides no suggestion that VPA may inhibit the action of PAI-1 and, therefore, does not suggest the administration of VPA to counteract (i.e. reduce) peak levels of PAI-1, thus providing a treatment (i.e. an improved treatment) for pathological conditions associated with excess fibrin deposition and/or thrombus formation.

US2007/0232528A1 describes controlled release formulations comprising valproic acid for use in the treatment of disorders such as cancer. These disclosures do not suggest the administration of VPA to counteract peak levels of PAI-1, for the treatment for pathological conditions associated with excess fibrin deposition and/or thrombus formation, and so do not suggest formulations designed for this use.

DESCRIPTION OF THE INVENTION

The present invention relates to fibrin degradation or breakdown (also called fibrinolysis), and more particularly compositions and methods for the treatment of pathological conditions associated with excess fibrin deposition and/or thrombus formation (e.g. thrombus formation).

In particular, the present invention relates to methods of using valproic acid, or pharmaceutically acceptable salts thereof, in the treatment or prevention of pathological conditions associated with excess fibrin deposition and/or thrombus formation.

The present invention also provides pharmaceutical compositions formulated to delay the release of valproic acid, or pharmaceutically acceptable salts thereof, in a manner suitable for use in such methods.

Medical Treatments

As described herein, it has been found that valproic acid, or pharmaceutically acceptable salts thereof, is able to inhibit the activity of PAI-1 (e.g. through reduction of PAI-1 levels), which itself is an inhibitor of t-PA. As a consequence, valproic acid, or pharmaceutically acceptable salts thereof, is able to increase the effects of t-PA and, therefore, is of use in the treatment or prevention of pathological conditions associated with excess fibrin deposition and/or thrombus formation.

In particular, the inventors have unexpectedly found that human subjects treated with VPA had reduced circulating levels of PAI-1. In healthy men circulating plasma levels of PAI-1 were significantly reduced by more than 50% after VPA treatment and in patients with coronary atherosclerosis by about 45%, which results are further described in Example 1 as provided herein.

The finding that VPA treatment lowers plasma levels of PAI-1 in man was unexpected given that in vitro data from cultured endothelial cells (one of the believed producers of plasma PAI-1) did not show a decrease of PAI-1 mRNA levels after VPA treatment, rather a slight but significant 30% increase in PAI-1 production. These studies also did not detect any effects of VPA on plasma PAI-1 in the in vivo models in pig (Svennerholm et al., PLoS One. 2014 May 12; 9 (5):e97260. doi: 10.1371/journal.pone.0097260. eCollection 2014) or in mouse (unpublished data).

In a first aspect of the invention, there is provided valproic acid, or a pharmaceutically acceptable salt thereof, for use in treating or preventing a pathological condition associated with excess fibrin deposition and/or thrombus formation, wherein said treatment comprises administering at least one dose of valproic acid, or a pharmaceutically acceptable salt thereof, to a patient such that the maximum plasma concentration (Cmax) of valproic acid, or a salt and/or metabolite thereof, in the patient occurs during a time period that is from four hours before to one hour after the maximum plasma concentration (Cmax) of PAI-1 in the patient.

In an alternative first aspect of the invention, there is provided the use of valproic acid, or a pharmaceutically acceptable salt thereof, in the manufacture of a medicament for use in treating or preventing a pathological condition associated with excess fibrin deposition and/or thrombus formation, wherein said treatment comprises administering at least one dose of valproic acid, or a pharmaceutically acceptable salt thereof, to a patient such that the maximum plasma concentration (Cmax) of valproic acid, or a salt and/or metabolite thereof, in the patient occurs during a time period that is from four hours before to one hour after the maximum plasma concentration (Cmax) of PAI-1 in the patient.

In a further alternative first aspect of the invention, there is a method of treating or preventing a pathological condition associated with excess fibrin deposition and/or thrombus formation in a patient in need thereof comprising administering at least one dose of a therapeutically effective amount of valproic acid, or a pharmaceutically acceptable salt thereof, to a patient such that the maximum plasma concentration (Cmax) of valproic acid, or a salt and/or metabolite thereof, in the patient occurs during a time period that is from four hours before to one hour after the maximum plasma concentration (Cmax) of PAI-1 in the patient.

The skilled person will understand that references herein to embodiments of particular aspects of the invention will include references to all other embodiments of those aspects of the invention. As such, any more or more embodiments of any aspect of the invention may be combined with any one or more other such embodiments in order to form more particular embodiments without departing from the disclosure of the invention as provided herein.

As used herein, references to a pathological condition associated with excess fibrin deposition and/or thrombus formation will refer in particular to pathological conditions associated with thrombus formation.

In a particular embodiment of the first aspect of the invention, the maximum plasma concentration (Cmax) of valproic acid, or a salt and/or metabolite thereof, in the patient occurs during a time period that is from four hours before to the time of the maximum plasma concentration (Cmax) of PAI-1 in the patient.

In another particular embodiment of the first aspect of the invention, the maximum plasma concentration (Cmax) of valproic acid, or a salt and/or metabolite thereof, in the patient occurs during a time period that is from three hours before (e.g. two hours before) to one hour after the maximum plasma concentration (Cmax) of PAI-1 in the patient.

In a more particular embodiment of the first aspect of the invention, the maximum plasma concentration (Cmax) of valproic acid, or a salt and/or metabolite thereof, in the patient occurs during a time period that is from three hours before (e.g. two hours before) to the time of the maximum plasma concentration (Cmax) of PAI-1 in the patient.

In a second aspect of the invention, there is provided valproic acid, or a pharmaceutically acceptable salt thereof, for use in treating or preventing a pathological condition associated with excess fibrin deposition and/or thrombus formation, wherein said treatment comprises administering at least one dose of Valproic acid, or a pharmaceutically acceptable salt thereof, to a patient such that at the time when the patient experiences the maximum plasma concentration (Cmax) of PAI-1, the patient has a plasma concentration of valproic acid, or a salt and/or metabolite thereof, that is at least about 10 to about 100 µg/ml, such as at least about 10 (e.g. at least about 20, about 30, about 40, about 50, about 60, about 70, about 80, about 90 or about 100 µg/ml).

In an alternative second aspect of the invention, there is provided the use of valproic acid, or a pharmaceutically acceptable salt thereof, in the manufacture of a medicament for use in treating or preventing a pathological condition associated with excess fibrin deposition and/or thrombus formation, wherein said treatment comprises administering at least one dose of Valproic acid, or a pharmaceutically acceptable salt thereof, to a patient such that at the time when the patient experiences the maximum plasma concentration (Cmax) of PAI-1, the patient has a plasma concentration of valproic acid, or a salt and/or metabolite thereof, that is at least about 10 to about 100 µg/ml, such as e.g. at least about 10, about 20, about 30, about 40, about 50, about 60, about 70, about 80, about 90 or about 100 µg/ml).

In a further alternative second aspect of the invention, there is provided a method of treating or preventing a pathological condition associated with excess fibrin deposition in a patient in need thereof comprising administering at least one therapeutically effective dose of valproic acid, or a pharmaceutically acceptable salt thereof, to a patient such that at the time when the patient experiences the maximum plasma concentration (Cmax) of PAI-1, the patient has a plasma concentration of valproic acid, or a salt and/or metabolite thereof, that is at least about 10 to about 100 μg/ml, such as e.g. at least about 10, about 20, about 30, about 40, about 50, about 60, about 70, about 80, about 90 or about 100 μg/ml).

For the avoidance of doubt, the skilled person will understand that references to compounds of the invention as provided herein above will apply to the second aspect of the invention (and alternative aspects and/or particular embodiments thereof) in the same manner as they apply to all other aspects of the invention described herein (and alternative aspects and/or particular embodiments thereof).

As used herein, the term therapeutic window will be understood to refer to plasma levels of the relevant compound, or a salt and/or metabolite thereof, at which the relevant (i.e. normally associated) therapeutic effect of that compound will typically be observed. The term may refer to a range of plasma levels or to a specific plasma level.

As used herein, the reference to an amount per millilitre (/ml) will be understood to refer to an amount per millilitre of plasma (i.e. blood plasma of the patient). As used herein, the reference to molar concentration will be understood to refer to a concentration in plasma (i.e. blood plasma of the patient).

In alternative second aspects of the invention, the patient has a plasma concentration of valproic acid, or a salt and/or metabolite thereof, that is below about 50 to about 170 μg/ml (such as e.g. below about 50, about 70, about 90, about 110, about 130, about 150, or about 170 μg/ml).

In further alternative second aspects of the invention, the patient has a plasma concentration of valproic acid, or a salt and/or metabolite thereof, that is at least about 70 to about 700 μM (such as e.g. at least about 70, about 140, about 210, about 280, about 350, about 420, about 490, about 560, about 630 or about 700 μM).

In yet further alternative second aspects of the invention, the patient has a plasma concentration of valproic acid, or a salt and/or metabolite thereof, that is below about 350 to about 1200 μM (such as e.g. below about 350, about 490, about 630, about 770, about 910, about 1050, or about 1190 μM).

For the avoidance of doubt, the skilled person will understand that references to certain maximum amounts and concentrations in plasma in the second aspect of the invention may also require a minimum of a therapeutically effective amount in said plasma.

In particular, the skilled person will understand that references to certain maximum (i.e. where values are indicated as being "below") and minimum (i.e. where values are indicated as being "at least") amount and/or concentrations in plasma may be combined to form ranges (i.e. wherein the amount in plasma is in a range that is from the minimum value to the maximum value).

For example, in one embodiment of the second aspect of the invention, the patient has a plasma concentration of valproic acid, or a salt and/or metabolite thereof, that is about 10 to about 170 μg/ml.

In other such embodiments, the patient has a plasma concentration of valproic acid, or a salt and/or metabolite thereof, that is:
from about 10 to about 70 ug/ml (or from about 50 to about 90, about 70 to about 110, about 90 to about 130, about 110 to about 150, about 130 to about 170, or about 150 to about 190 ug/ml);
from about 10 to about 50 ug/ml (or from about 10 and to about 100, about 30 to about, about 50 to about 170, or about 70 to about 190 ug/ml);
from about 30 to about 190 ug/ml (e.g. about 50 to about 170, about 70 to about 150, about 90 to about 130, about 30 to about 110, about 50 to about 130, or about 70 to about 170 ug/ml).

The skilled person will understand that references to certain minimum plasma levels herein (e.g. in the second aspect of the invention) will include references to such levels at a time when the patient has reached a steady state of valproic acid, or a salt and/or metabolite thereof, in plasma. Moreover, the skilled person will understand that references to the patient reaching a steady state may refer to the plasma levels achieved after said patient has been treated with compounds of the invention (at a therapeutically-effective dose thereof) for at least two to five days (e.g. at least five days).

The skilled person will also understand that the references to maximum and minimum plasma levels in the second aspect of the invention (including all embodiments and alternative aspects thereof) may also apply to the plasma levels observed for the Cmax of valproic acid, or a salt and/or metabolite thereof, as referred to in other aspects of the invention (such as the first aspect of the invention).

In a third aspect of the invention, there is provided valproic acid, or a pharmaceutically acceptable salt thereof, for use in treating or preventing a pathological condition associated with excess fibrin deposition and/or thrombus formation, wherein said treatment comprises administering a dose of valproic acid, or a pharmaceutically acceptable salt thereof, to a patient during a time period from about 20:00 hours to about 06:00 hours.

In an alternative third aspect of the invention, there is provided the use of valproic acid, or a pharmaceutically acceptable salt thereof, in the manufacture of a medicament for use in treating or preventing a pathological condition associated with excess fibrin deposition and/or thrombus formation, wherein said treatment comprises administering a dose of valproic acid, or a pharmaceutically acceptable salt thereof, to a patient during a time period from about 20:00 hours to about 06:00 hours.

In a further alternative third aspect of the invention, there is provided a method of treating or preventing a pathological condition associated with excess fibrin deposition and/or thrombus formation in a patient in need thereof comprising administering a therapeutically effective dose of valproic acid, or a pharmaceutically acceptable salt thereof, to a patient during a time period from about 20:00 hours to about 06:00 hours.

In a particular embodiment of the third aspect of the invention, the treatment comprises administering a therapeutically effective dose of valproic acid, or a pharmaceutically acceptable salt thereof, to a patient during a time period from about 21:00 hours to about 05:00 hours (e.g. about 22:00 hours to about 04:00 hours).

The skilled person will understand that timings referred to using the 24-hour system may also be referred to as timings using the 12-hour system (i.e. with AM and PM denoting times before and after 12:00 noon, respectively). For example, 20:00 may also be referred to as 8:00 PM, and 06:00 as 6:00 AM.

In a particular embodiment of the third aspect of the invention (particularly wherein the treatment is administered as a pharmaceutical composition that is not formulated for delayed release of the active ingredient), the treatment comprises administering a therapeutically effective dose of valproic acid, or a pharmaceutically acceptable salt thereof, to a patient during a time period from about 02:00 hours to about 06:00 hours (e.g. about 03:00 hours to about 05:00 hours, such as about 04:00 hours).

In another particular embodiment of the third aspect of the invention (particularly wherein the treatment is administered as a pharmaceutical composition that is formulated for delayed release of the active ingredient, such as those described in the eight aspect of the invention herein), the treatment comprises administering a therapeutically effective dose of valproic acid, or a pharmaceutically acceptable salt thereof, to a patient during a time period from about 20:00 hours to about 00:00 hours (e.g. about 21:00 hours to about 23:00 hours, such as at about 22:00 hours).

In alternative embodiments of the third aspect of the invention, the treatment comprises administering a therapeutically effective dose of valproic acid, or a pharmaceutically acceptable salt thereof, to a patient during a time period determined based on the release profile of that formulation in order to provide a plasma concentration of valproic acid, or a salt and/or metabolite thereof, as required in the first and/or second aspect of the invention.

As described herein, the skilled person will be able to determine how to administer compounds of the invention in a manner (e.g. during a certain time period) in order to achieve parameters described herein (such as those described in the first and second aspects of the invention).

For the avoidance of doubt, in particular embodiments of the third aspect of the invention, the dose referred to is a single dose, which will indicate that the dose is the only dose of the compound given to the patient during a (e.g. the relevant) 24 hour period.

In a fourth aspect of invention, there is provided valproic acid, or a pharmaceutically acceptable salt thereof, for use in treating or preventing a pathological condition associated with excess fibrin deposition and/or thrombus formation, wherein said treatment comprises administering a pharmaceutical composition comprising a dose of valproic acid, or a pharmaceutically acceptable salt thereof, to a patient at a time and in a form such that substantially all of the valproic acid, or a pharmaceutically acceptable salt thereof, is released from the composition during a time period from about 02:00 hours to about 06:00 hours.

In an alternative fourth aspect of invention, there is provided the use of valproic acid, or a pharmaceutically acceptable salt thereof, in the manufacture of a medicament for use in treating or preventing a pathological condition associated with excess fibrin deposition and/or thrombus formation, wherein said treatment comprises administering a pharmaceutical composition comprising a dose of valproic acid, or a pharmaceutically acceptable salt thereof, to a patient at a time and in a form such that substantially all of the valproic acid, or a pharmaceutically acceptable salt thereof, is released from the composition during a time period from about 02:00 hours to about 06:00 hours.

In a further alternative fourth aspect of invention, there is provided a method of treating or preventing a pathological condition associated with excess fibrin deposition and/or thrombus formation in a patient in need thereof comprising administering a pharmaceutical composition comprising a therapeutically effective dose of valproic acid, or a pharmaceutically acceptable salt thereof, to a patient at a time and in a form such that substantially all of the valproic acid, or a pharmaceutically acceptable salt thereof, is released from the composition during a time period from about 02:00 hours to about 06:00 hours.

In a particular embodiment of the fourth aspect of the invention, the treatment comprises administering a pharmaceutical composition comprising a therapeutically effective dose of valproic acid, or a pharmaceutically acceptable salt thereof, to a patient at a time and in a form such that substantially all of the valproic acid, or a pharmaceutically acceptable salt thereof, is released from the composition during a time period from about 03:00 hours to about 05:00 hours (e.g. from about 04:00 hours to about 05:00 hours, such as at about 05:00 hours).

In a particular embodiment of the fourth aspect of the invention, the treatment comprises administering a pharmaceutical composition as described in the eight aspect of the invention herein below (including all embodiments thereof).

In a fifth aspect of the invention, there is provided valproic acid, or a pharmaceutically acceptable salt thereof, for use in treating or preventing a pathological condition associated with excess fibrin deposition and/or thrombus formation in a patient, wherein said treatment comprises:
 (i) monitoring the plasma concentration of PAI-1 in the patient in order to determine the time at, or time period during which, the maximum plasma concentration of PAI-1 occurs;
 (ii) administering at least one dose of valproic acid, or a pharmaceutically acceptable salt thereof, to the patient such that the maximum plasma concentration (Cmax) of valproic acid, or a salt and/or metabolite thereof, in the patient occurs during a time period that is from four hours before to one hour after the time at which, or time period during which, the maximum plasma concentration of PAI-1 occurs.

In an alternative fifth aspect of the invention, there is provided the use of valproic acid, or a pharmaceutically acceptable salt thereof, in the manufacture of a medicament for use in treating or preventing a pathological condition associated with excess fibrin deposition and/or thrombus formation in a patient, wherein said treatment comprises:
 (i) monitoring the plasma concentration of PAI-1 in the patient in order to determine the time at, or time period during which, the maximum plasma concentration of PAI-1 occurs; and
 (ii) administering at least one dose of valproic acid, or a pharmaceutically acceptable salt thereof, to the patient such that the maximum plasma concentration (Cmax) of valproic acid, or a salt and/or metabolite thereof, in the patient occurs during a time period that is from four hours before to one hour after the time at which, or time period during which, the maximum plasma concentration of PAI-1 occurs.

In a further alternative fifth aspect of the invention, there is provided a method of treating or preventing a pathological condition associated with excess fibrin deposition and/or thrombus formation in a patient in need thereof comprising the steps of:
 (i) monitoring the plasma concentration of PAI-1 in the patient in order to determine the time at, or time period during which, the maximum plasma concentration of PAI-1 occurs; and
 (ii) administering at least one therapeutically effective dose of valproic acid, or a pharmaceutically acceptable salt thereof, to the patient such that the maximum plasma concentration (Cmax) of valproic acid, or a salt and/or metabolite thereof, in the patient occurs during a time period that is from four hours before to one hour after the time at which, or time period during which, the maximum plasma concentration of PAI-1 occurs.

As described herein, plasma concentrations of PAI-1 may be monitored using techniques well-known to those skilled in the art. For instance, PAI-1 levels are generally measured in plasma. Blood may be collected from an antecubital syringe regularly e.g. every hour, every second hour or every third hour throughout 24 hours. The blood samples are immediately centrifuged to separate plasma from the serum. Thereafter PAI-1 levels in plasma are determined by using commercially available ELISA-kits, such as Coaliza® PAI-1 (Chromogenix), TriniLIZE® PAI-1 (Trinity Biotech), Imubind® Plasma PAI-1 (American Diagnostica), Zymutest PAI-1 (Hyphen Biomed), Milliplex PAI-1 (MerckMillipore), Novex PAI-1 human Elisa kit (Life technology), PAH (SERPINE1) Human ELISA Kit (Abcam, ab108891).

In a particular embodiment of the fifth aspect of the invention, the maximum plasma concentration (Cmax) of valproic acid, or a salt and/or metabolite thereof, in the patient occurs during a time period that is from four hours before (e.g. three hours before, such as 2 hours before or 1 hour before or 0.5 hours before) to the time of the maximum plasma concentration (Cmax) of PAI-1 in the patient.

In another particular embodiment of the fifth aspect of the invention, the maximum plasma concentration (Cmax) of valproic acid, or a salt and/or metabolite thereof, in the patient occurs during a time period that is from three hours before (e.g. two hours before) to one hour after the maximum plasma concentration (Cmax) of PAI-1 in the patient.

In a more particular embodiment of the fifth aspect of the invention, the maximum plasma concentration (Cmax) of valproic acid, or a salt and/or metabolite thereof, in the patient occurs during a time period that is from three hours before (e.g. two hours before) to the time of the maximum plasma concentration (Cmax) of PAI-1 in the patient.

The skilled person will understand that the timing and level of the Cmax of VPA will depend on the dose administered (and, to some extent, the form in which that dose is administered). The skilled person will be able to measure the plasma concentration of VPA, or a metabolite and/or salt thereof, and determine the timing and level of the Cmax (and, if necessary, to adjust the dose and form of VPA accordingly). Particular doses (i.e. therapeutic doses) of VPA that may be administered and Cmax levels that may be obtained include those as described herein.

In a sixth aspect of the invention, there is provided valproic acid, or a pharmaceutically acceptable salt thereof, for use in treating or preventing a pathological condition associated with excess fibrin deposition and/or thrombus formation in a patient, wherein said treatment comprises:
(i) monitoring the plasma concentration of PAI-1 in the patient in order to determine the time at, or time period during which, the maximum plasma concentration of PAI-1 occurs; and
(ii) administering at least one dose of valproic acid, or a pharmaceutically acceptable salt thereof, to the patient such that at the time when the patient experiences the maximum plasma concentration of PAI-1, the patient has a plasma concentration of valproic acid, or a salt and/or metabolite thereof, that is at least about 10 to about 100 µg/ml (such as e.g. at least about 10, about 20, about 30, about 40, about 50, about 60, about 70, about 80, about 90 or about 100 µg/ml).

In an alternative sixth aspect of the invention, there is provided the use of valproic acid, or a pharmaceutically acceptable salt thereof, in the manufacture of a medicament for use in treating or preventing a pathological condition associated with excess fibrin deposition and/or thrombus formation in a patient, wherein said treatment comprises:
(i) monitoring the plasma concentration of PAI-1 in the patient in order to determine the time at, or time period during which, the maximum plasma concentration of PAI-1 occurs; and
(ii) administering at least one dose of valproic acid, or a pharmaceutically acceptable salt thereof, to the patient such that at the time when the patient experiences the maximum plasma concentration of PAI-1, the patient has a plasma concentration of valproic acid, or a salt and/or metabolite thereof, that is at least about 10 to about 100 µg/ml (such as e.g. at least about 10, about 20, about 30, about 40, about 50, about 60, about 70, about 80, about 90 or about 100 µg/ml).

In a further alternative sixth aspect of the invention, there is provided a method of treating or preventing a pathological condition associated with excess fibrin deposition and/or thrombus formation in a patient in need thereof comprising the steps of:
(i) monitoring the plasma concentration of PAI-1 in the patient in order to determine the time at, or time period during which, the maximum plasma concentration of PAI-1 occurs; and
(ii) administering at least one therapeutically effective dose of valproic acid, or a pharmaceutically acceptable salt thereof, to the patient such that at the time when the patient experiences the maximum plasma concentration of PAI-1, the patient has a plasma concentration of valproic acid, or a salt and/or metabolite thereof, that is at least about 10 to about 100 µg/ml (such as e.g. at least about 10, about 20, about 30, about 40, about 50, about 60, about 70, about 80, about 90 or about 100 µg/ml).

In alternative sixth aspects of the invention, the patient has a plasma concentration of valproic acid, or a salt and/or metabolite thereof, that is below about 50 to about 170 µg/ml (such as e.g. below about 50, about 70, about 90, about 110, about 130, about 150, or about 170 µg/ml).

In further alternative sixth aspects of the invention, the patient has a plasma concentration of valproic acid, or a salt and/or metabolite thereof, that is at least about 70 to about 700 µM (such as e.g. at least about 70, about 140, about 210, about 280, about 350, about 420, about 490, about 560, about 630 or about 700 µM).

In yet further alternative sixth aspects of the invention, the patient has a plasma concentration of valproic acid, or a salt and/or metabolite thereof, that is below about 350 to about 1200 µM (such as e.g. below about 350, about 490, about 630, about 770, about 910, about 1050, or about 1190 µM).

For the avoidance of doubt, the skilled person will understand that references herein to levels and concentrations (e.g. plasma levels and plasma concentrations) of "valproic acid, or a salt and/or metabolite thereof" will refer in particular to levels and concentrations (e.g. plasma levels and plasma concentrations) of valproic acid.

Again, the skilled person will understand that references to certain maximum amounts and concentrations in plasma in the sixth aspect of the invention may also require a minimum of a therapeutically effective amount in said plasma. Moreover, the skilled person will understand that references to certain maximum (i.e. where values are indicated as being "below") and minimum (i.e. where values are indicated as being "at least") amount and/or concentrations in plasma may be combined to form ranges (i.e. wherein the amount in plasma is in a range that is from the minimum value to the maximum value).

For example, in one embodiment of the sixth aspect of the invention, the patient has a plasma concentration of valproic acid, or a salt and/or metabolite thereof, that is about 10 to about 170 µg/ml. In other such embodiments, the patient has a plasma concentration of valproic acid, or a salt and/or metabolite thereof, that is:

from about 10 to about 70 ug/ml (or from about 50 to about 90, about 70 to about 110, about 90 to about 130, about 110 to about 150, about 130 to about 170, or about 150 to about 190 ug/ml);

from about 10 to about 50 ug/ml (e.g. from about 10 and to about 100, about 30 to about, about 50 to about 170, or about 70 to about 190 ug/ml);

from about 30 to about 190 ug/ml (e.g. about 50 to about 170, about 70 to about 150, about 90 to about 130, about 30 to about 110, about 50 to about 130, or about 70 to about 170 ug/ml).

In a seventh aspect of the invention, there is provided valproic acid, or a pharmaceutically acceptable salt thereof, for use in treating or preventing a pathological condition associated with excess fibrin deposition and/or thrombus formation, wherein said treatment comprises administering a single dose of valproic acid, or a pharmaceutically acceptable salt thereof, to a patient in a 24 hour period, wherein the dose is from about 50 mg to about 1000 mg (such as about 200 mg to about 600 mg).

In an alternative seventh aspect of the invention, there is provided the use of valproic acid, or a pharmaceutically acceptable salt thereof, in the manufacture of a medicament for use in treating or preventing a pathological condition associated with excess fibrin deposition and/or thrombus formation, wherein said treatment comprises administering a single dose of valproic acid, or a pharmaceutically acceptable salt thereof, to a patient in a 24 hour period, wherein the dose is from about 50 mg to about 1000 mg (such as about 200 mg to about 600 mg).

In a further alternative seventh aspect of the invention, there is provided a method of treating or preventing a pathological condition associated with excess fibrin deposition and/or thrombus formation in a patient in need thereof comprising administering a single, therapeutically effective dose of valproic acid, or a pharmaceutically acceptable salt thereof, to a patient in a 24 hour period, wherein the dose is from about 50 mg to about 1000 mg (such as about 200 mg to about 600 mg).

Unless otherwise stated or apparent from the context (e.g. when discussed in reference to a specific formulation), references to the dose of compounds of the invention (e.g. the dose of valproic acid or a pharmaceutically acceptable salt thereof) will be understood to refer to the dose of valproic acid (i.e. the dose of valproic acid itself, or the effective (i.e. equivalent) dose of valprioic acid when administered in the form that includes or consists of one or more salt thereof.

In a particular embodiment of the seventh aspect of the invention, the dose is from about 200 mg to about 400 mg, such as about 400 or about 300 mg. In another particular embodiment of the seventh aspect of the invention, the dose is from about 300 mg to about 500 mg, such as about 350 mg. In another particular embodiment of the seventh aspect of the invention, the dose is from about 400 mg to about 600 mg, such as about 450 or about 550 mg. In another particular embodiment of the seventh aspect of the invention, the dose is from about 400 mg to about 800 mg, such as about 575, about 650 or about 700 mg.

Again, for the avoidance of doubt, all references herein to particular aspects of the invention (e.g. the first aspect of the invention) will include references to all alternative such aspects of the invention (e.g. the alternative and further alternative first aspects of the invention).

Moreover, the skilled person will understand that all embodiments, preferences, particular definitions and the like referred to herein may be combined with any one or more other embodiments, preferences, particular definitions and the like also referred to herein.

When used herein in reference to a value or an amount (including an amount of time), the terms "about", "around" and "approximately" will be understood as referring to a value that is within 10% of the value defined. When used herein in reference to a specific point in time (including the start or end of a period of time), the terms "about" and "around" will be understood as referring to a value that is within 30 minutes (e.g. within 20 minutes, such as within 10 minutes) of that specific time. Further, it is contemplated that each reference to the terms "about", "around" and "approximately" (e.g. in relation to times and amounts) may be deleted throughout.

As used herein, the term "compounds of the invention" will refer to valproic acid and pharmaceutically acceptable salts thereof. The skilled person will understand that references to valproic acid and pharmaceutically acceptable salts thereof (e.g. references to "valproic acid, or a pharmaceutically acceptable salt thereof") may include references to mixtures of different pharmaceutically acceptable salts, and references to mixtures of valproic acid (i.e. in non-salt form) and pharmaceutically acceptable salts thereof (including mixtures of such salts), all of which may be referred to as compounds of the invention.

As used herein, the skilled person will understand that references to "preventing" a particular condition may also be referred to as "prophylaxis" of said condition, and vice versa. Thus, each reference herein to "preventing" a condition may be replaced with a reference to "prophylaxis" of said condition.

The skilled person will understand that the terms "treatment" and "treating" when used herein take their normal meanings in the field of medicine. In particular, these terms may refer to achieving a reduction in the severity of one or more clinical symptom associated with the relevant condition.

The skilled person will also understand that the terms "prevention" and "preventing" when used herein take their normal meanings in the field of medicine. In particular, these terms may refer to achieving a reduction in the likelihood of (the patient) developing the relevant condition (for example, a reduction of at least 10% when compared to the baseline level, such as a reduction of at least 20% or, more particularly, a reduction of at least 30%).

The skilled person will also understand that references to prophylaxsis (or prevention) of a particular condition may also include the treatment of another condition. For example, treatment of a primary condition may also be considered to be a form of prophylaxsis of a secondary condition.

In particular embodiments of the first to seventh aspects of the invention (including all alternative aspects), there are provided compounds for use in (and/or uses in and/or methods for) preventing a pathological condition associated with excess fibrin deposition and/or thrombus formation (particularly, thrombus formation).

As used herein, the term "pathological conditions" will be understood to refer to identifiable diseases or disorders.

As described herein, pathological conditions that may be treated or prevented in accordance with the invention associated with excess fibrin deposition and/or thrombus formation. These include, but are not limited to, atherosclerosis, myocardial infarction, ischemic stroke, deep vein thrombosis, superficial vein thrombosis, thrombophlebitis, pulmonary embolism, disseminated intravascular coagulation, renal vascular disease and intermittent claudication (e.g. atherosclerosis, myocardial infarction, ischemic stroke, deep vein thrombosis, pulmonary embolism, disseminated intravascular coagulation, renal vascular disease and intermittent claudication).

Thus, in particular embodiments of the first to seventh aspects of the invention, the pathological condition associated with excess fibrin deposition and/or thrombus formation is selected from the group consisting of atherosclerosis, myocardial infarction, ischemic stroke, deep vein thrombosis, pulmonary embolism, disseminated intravascular coagulation, renal vascular disease and intermittent claudication.

Thus, in more particular embodiments of the first to seventh aspects of the invention, the pathological condition associated with excess fibrin deposition and/or thrombus formation is selected from the group consisting of myocardial infarction, ischemic stroke and pulmonary embolism.

In other more particular embodiments of the first to seventh aspects of the invention, the pathological condition associated with excess fibrin deposition and/or thrombus formation is selected from the group consisting of myocardial infarction and ischemic stroke (such as myocardial infarction).

The skilled person will understand that references to ischemic stroke include references to major stroke events (i.e. those caused by prolonged impairment of blood flow), minor strokes and transient ischemic attacks (TIAs).

Thus, in more particular embodiments of the first to seventh aspects of the invention, the pathological condition associated with excess fibrin deposition and/or thrombus formation is ischemic stroke, such as a major ischemic stroke, minor ischemic stroke or a TIA.

In even more particular embodiments of the first to seventh aspects of the invention, the pathological condition associated with excess fibrin deposition and/or thrombus formation is ischemic stroke, such as a major ischemic stroke and minor ischemic stroke.

In particular, it is believed that compounds of the invention, when administered in accordance with the dosage regimes defined above (e.g. in the first to seventh aspects of the invention), may be of particular use in preventing a pathological condition associated with excess fibrin deposition and/or thrombus formation (such as ischemic stroke and/or myocardial infarction). Thus, all references to treating and preventing such conditions herein will include particular references to preventing such conditions.

Thus, in yet more particular embodiments of the first to seventh aspects of the invention, treating or preventing a pathological condition associated with excess fibrin deposition and/or thrombus formation will refer to preventing ischemic stroke, such as a major ischemic stroke, minor ischemic stroke or a TIA.

As discussed above, thrombotic cardiovascular events occur as a result of two distinct processes, i.e. a slowly progressing long-term vascular atherosclerosis of the vessel wall, on the one hand, and a sudden acute clot formation that rapidly causes flow arrest, on the other. Particular pathological conditions that may be treated are those relating to the latter process.

In particular embodiments of the first to seventh aspects of the invention, pathological conditions that may be treated or prevented in accordance with the invention are those that are caused wholly or at least in part by an increased fibrin deposition and/or reduced fibrinolytic capacity due to local or systemic inflammation. These include, but are not limited to, myocardial infarction, stable angina pectoris, unstable angina pectoris, intermittent claudication, ischemic stroke, transient ischemic attack, deep vein thrombosis and pulmonary embolism. These conditions may display elevated PAI-1 levels in plasma.

In particular embodiments of the first to seventh aspects of the invention, the pathological condition may be selected from the group consisting of deep vein thrombosis and pulmonary embolism.

In particular embodiments of the first to seventh aspects of the invention, the pathological condition is deep vein thrombosis.

In particular embodiments of the first to seventh aspects of the invention, the pathological condition may be selected from the group consisting of superficial vein thrombosis and thrombophlebitis.

In more particular embodiments of the first to seventh aspects of the invention, the pathological condition is superficial vein thrombosis.

In more particular embodiments of the first to seventh aspects of the invention, the pathological condition is thrombophlebitis.

In addition, pathological conditions that can be treated in accordance with the invention are those that are caused wholly or at least in part by an increased fibrin deposition and/or reduced fibrinolytic capacity due to local or systemic inflammation. These include but are not limited to atherosclerosis, the metabolic syndrome, diabetes, disseminated intravascular coagulation, rheumatoid arthritis, glomerulo-nephritis, systematic lupus erythematosis, vasculitides, autoimmune neuropathies, and granulomatous disease as well as inflammation associated with other conditions (such as the metabolic syndrome, diabetes, disseminated intravascular coagulation, rheumatoid arthritis, glomerulo-nephritis, systematic lupus erythematosis, vasculitides, autoimmune neuropathies, and granulomatous disease as well as inflammation associated with other conditions).

In addition to traditional diagnosis of a systemic or local inflammation by a physician as is known in the art, a local or systemic inflammation can be determined in patients using one or more biomarkers coupled to inflammation. These biomarkers include, but are not limited to, C reactive protein, TNF-alpha, high sensitive C-reactive protein (hs-CRP), fibrinogen, IL-1beta, and IL-6. Particular methods for determining whether a patient has systemic or local inflammation include those described hereinafter.

In addition, atherosclerotic plaques are known to be associated with a very localized inflammatory process. Hence, local inflammation may also be indirectly determined by the presence of atherosclerotic plaques as diagnosed by vascular ultrasound or other imaging techniques.

The skilled person will understand that, to identify a poor level of fibrinolysis in a patient (i.e. reduced fibrinolytic capacity), there are a few different alternatives available. For example, high circulating levels of PAI-1 are generally considered to be indicative of poor fibrinolysis, and this can be measured in plasma by commercially available methods (including but not limited by Coaliza® PAI-1 (Chromgenix), TriniLIZE® PAI-1 (Trinity Biotech), Imubind® Plasma PAI-1 (American Diagnostica), Zymutest PAI-1 (Hyphen Biomed), Milliplex PAI-1 (MerckMillipore), Novex PAI-1 human Elisa kit (Life technology), PAI1 (SERPINE1) Human ELISA Kit (Abcam, ab108891)). Further, low systemic levels of free, active t-PA is also an indicator of general poor fibrinolysis and can also be measured by commercial methods (TriniLIZE® t-PA antigen and activity (Trinity Biotech), as is the presence of a low-producer (T)

genotype of the t-PA-7351 C/T polymorphism. Functional assays measuring clot lysis time have also been used to assess global fibrinolysis (Thrombinoscope™ (Synapse, BV, Maastricht, the Netherlands), IL/ROTEM® (Term International GmbH, Munich, Germany), TEG® (Haemoscope, Niles), CloFAL assay (Peikang Biotechnology Co. Ltd. Shanghai, China)).

The skilled person will understand that whether the increased fibrin deposition and/or reduced fibrinolytic capacity is due to "local or systemic inflammation" as used herein can be determined using one or more biomarkers coupled to inflammation, including but not limited to C reactive protein, TNF-alpha, high sensitive C-reactive protein (hs-CRP), fibrinogen, IL-1beta, and IL-6 (e.g. by increased concentration of one or more of these biomarkers in relation to control levels as known in the art). Commercial analytical platforms that can be used to quantify these biomarkers include, but are not limited to, Afinion™ (Medinor AB, Sweden), CA-7000 (Siemens Healthcare Diagnostics Inc, NY, US), Immulite® 2000 Immunoassay System (Siemens Healthcare Diagnostics Inc).

Particular biomarkers that may identify local or systemic inflammation include high sensitive C-reactive protein (hs-CRP) (at or above 2.0 mg/l serum) and fibrinogen (at or above 3 g/l serum) (Corrado E., et al. An update on the role of markers of inflammation in atherosclerosis, Journal of atherosclerosis and Thrombosis, 2010; 17:1-11, Koenig W., Fibrin(ogen) in cardiovascular disease: an update, Thrombosis Haemostasis 2003; 89:601-9).

Unless otherwise specified, as used herein, the term "patient" includes mammalian patients (such as equines, cattle, swine, sheep, goats, primates, mice, rats, and pets in general including dogs, cats, guinea pigs, ferrets, and rabbits). In particular, the term "patient" refers to humans.

As used herein, the skilled person will understand that references to plasma will refer to the blood plasma of the patient.

As used herein, the skilled person will understand that references to the maximum plasma concentration (or "Cmax") of a particular substances will refer to the maximum concentration of that agent in blood plasma (i.e. the blood plasma of the patient). In the context of the administration of that agent, the Cmax will refer to that occurring as a direct result of such administration (i.e. the Cmax occurring as a result of the absorption of that agent).

As used herein, the time at which the Cmax of a particular substance occurs may also be referred to as the Tmax.

The skilled person will understand that the Cmax may occur at a specific time (i.e. a particular peak in plasma concentration) or for a prolonged period (i.e. where the plasma concentration reaches a plateau), both of which may be referred to as the time at which the Cmax occurs (the Tmax). Where the Cmax occurs for a prolonged period, the time at which the Cmax occurs may also be taken to the mid-point of that period, although it is generally understood that the Cmax will occur as a clearly distinguishable peak at a specific time.

As described herein, the plasma concentration of PAI-1 in a patient (particularly a human) is known to follow a circadian rhythm. Typically, the maximum plasma concentration (Cmax) of PAI-1 is expected to occur at around 06:00 hours.

Thus, references herein to the time at which the Cmax of PAI-1 occurs may be replaced with a reference to about 06:00 hours.

All absolute times (i.e. specific points in time and periods defined as being between specific points in time) indicated herein refer to the actual local time (i.e. the 'clock' time) experienced by the patient. Moreover, said times assume that the patient is adjusted to local time (for example, having had adequate time to adjust to changes in time zone or so-called "daylight savings" time adjustments).

The skilled person will understand that the timing of the maximum plasma concentration of PAI-1 and compounds of the invention (or salts and/or metabolites thereof) may be determined using techniques that are well known to those skilled in the art, such as by monitoring the concentration of PAI-1 and compounds of the invention (or salts and/or metabolites thereof) in plasma during the relevant time period.

As described herein, plasma levels of compounds of the invention (or salts and/or metabolites thereof) may be monitored using techniques well-known to those skilled in the art. For example, valproate plasma levels are determined in clinical routine e.g. by using a homogeneous enzyme immunoassay technique, based on competition of antibodies between valproate in the sample and enzyme-labelled valproate added to the test (e.g. VALP2, Roche/Cobas, art nr 05108438190 (Roche Diagnostics Scandinavia AB). When the enzyme-labelled valproate is bound to the antibody, the enzyme Glucose 6-phosphate dehydrogenase, (G6PDH) is blocked and cannot consume the test enzyme substrate. Conversely, when the enzyme-labelled valproate is not bound to the antibody, the substrate is available to the enzyme and can be consumed. The consumption of the substrate is measured indirectly by formation of NADH from NAD (coenzyme reaction). NADH absorbs UV light selectively at 340 nm. This means that high valproate concentration in the sample gives a large change in absorbance at 340 nm; conversely at low valproate concentration, there may be a small change in absorbance at 340 nm. The consumption of substrate gives rise to a colour change that is measured photochromatically at 340 and 415 nm. The absorbance is directly proportional to the valproate concentration in the sample.

The skilled person will be able to identify compounds present in plasma as being metabolites of compounds of the invention. Particular metabolites of compounds of the invention that may be mentioned include the valproate anion (e.g. metabolites that comprise a valproate anion moiety).

The skilled person will understand that references to monitoring the plasma concentration (i.e. the blood plasma concentration in the patient) of PAI-1 may refer to monitoring over at least one (e.g. one) 24 hour period (e.g. prior to the beginning of treatment with compounds of the invention). Such monitoring may be continuous or may involve the taking of measurements at set intervals during this period (which may mean that, particularly in the latter case, the time between the first and last measurement is less than 24 hours, such as around 20 hours).

The skilled person will also understand that such monitoring may instead be conducting for a period of time that is expected to include the Cmax of PAI-1, as estimated by a person skilled in the art. For example, where the Cmax of PAI-1 is expected to occur at around 06:00 hours, such monitoring may take place at from 04:00 hours to 08:00 hours (e.g. from 05:00 hours to 07:00 hours).

The timing and size of the dose of compounds of the invention administered will also result in low plasma concentrations of valproic acid, or a salt and/or metabolite thereof, at specific times.

Thus, in a particular embodiment of the first to seventh aspects of the invention, administration of the compounds of the invention is such that the plasma concentration of valproic acid, or a salt and/or metabolite thereof, during the period from about 14:00 hours to about 18:00 hours (e.g. from about 15:00 hours to about 17:00, such as at about 16:00 hours) is less than about 350 µM (such as less than about 300 µM, for example less than about 250 µM or, more particularly, less than about 200 µM, such as less than about 150 µM or less than about 100 µM).

In a more particular embodiment of the first to seventh aspects of the invention, administration of the compounds of the invention is such that the plasma concentration of valproic acid, or a salt and/or metabolite thereof, during the period from about 15:00 hours to about 17:00 hours (such as at about 15:30 hours or about 16:30 hours) is less than about 300 µM (such as less than about 200 µM (e.g. less than about 150 µM, or less than about 100 µM).

Further, the skilled person will be able to adjust both the timing and dose of administration of compounds of the invention in order to meet the requirements of the timing of the Cmax and/or the presence of a maximum or minimum concentration in plasma at a specified time.

As used herein, the terms "therapeutically effective amount" and "therapeutically effective dose" refer to an amount of the active agent (i.e. the compounds of the invention) which confers the required pharmacological or therapeutic effect on the patient, preferably without undue adverse side effects. It is understood that the therapeutically effective amount may vary from patient to patient.

In particular, a therapeutically effective dose of a compound according to the present invention is an amount sufficient to treat or prevent the relevant pathological condition and its complications, particularly where selected to minimise side effects (i.e. adverse events brought about by the action of the therapeutic agent). In view of the disclosures herein, the skilled person will be able to adjust the dose of compounds of the invention administered in order to achieve the desired biological effect using techniques known to those skilled in the art.

The skilled person will understand that the dose of the compounds of the invention may be titrated such that a dose is determined that will achieve a reduction in PAI-1 plasma levels of at least about 20% (such as at least about 30%).

In particular embodiments of the invention (for example, particular embodiments of the first to seventh aspects of the invention), the dose of the compounds of the invention is sufficient to achieve a reduction in PAI-1 plasma levels of at least about 20% (such as at least about 30%), i.e. the dose is titrated to achieve the required reduction in plasma levels of PAI-1.

In more particular embodiments of the invention (for example, particular embodiments of the first to seventh aspects of the invention), the dose is sufficient to achieve a reduction in PAI-1 plasma levels of at least about 40% (such as at least about 50%, e.g. at least about 60%).

Similar dose titrations are known in the art and both starting dose, increments and intervals for PAI-1 measurements (generally from morning samples), desired reduction in PAI-1 and potential dose increments may be chosen by the person skilled in the art.

In certain embodiments, the starting doses for such dose titrations may be in the range of e.g. 50, 100, 150, 200, 250 or 300 mg and dose increments may be 20-100 mg every 7-28 days following a new PAI-1 measurement. For example, in one such measurement the starting dose for a dose titration is 50 mg and the dose is raised in increments of 50 mg every 7 days until a 20% reduction in circulating PAI-1 levels is achieved. In another such measurement, the starting dose for a dose titration is 100 mg and the dose is raised in increments of 100 mg every 14 days until a 20% reduction in circulating PAI-1 levels is achieved.

Without wishing to be bound by theory, it is thought that the surprising effects resulting from the administration of compounds of the invention as described herein can be obtained through administration of doses that are at a level that is not expected to result in significant levels of adverse events.

Thus, in particular embodiments of the first to seventh aspects of the invention, the treatment may require administering a dose of valproic acid or a pharmaceutically acceptable salt thereof (e.g. one such dose in a 24 hour period) that is selected in order to minimise the level of adverse events resulting from such treatment (e.g. is of a sufficiently low level to avoid the occurrence of such adverse events).

Such amounts may vary according to the frequency and mode of administration, the sex, age, weight and general condition of the subject treated, the nature and severity of the condition treated and or other treatments used by the individual, and may be determined by conventional techniques in the field. The amount that is effective for a particular therapeutic purpose will depend on the severity of the condition as well as on the weight and general state of the subject. It will be understood that determination of an appropriate dosage may be achieved, using routine experimentation, by constructing a matrix of values and testing different points in the matrix, all of which is within the ordinary skills of a person skilled in the art.

Notwithstanding the discussion of specific doses as provided herein, the skilled person will understand that the amounts of and dosage regimes of VPA, or a pharmaceutically acceptable salt thereof, required for treating or preventing a pathological condition associated with excess fibrin deposition and/or thrombus formation as described herein may be determined using the routine skill of the prescribing physician.

In particular embodiments of the first to seventh aspects of the invention, compounds of the invention may be administered:

(i) as a single dose per 24 hour period (i.e. a single daily dose); and/or (ii) at a total dose per 24 hour period (i.e. a total daily dose) of about 50 mg to about 1000 mg (particularly about 200 mg to about 600 mg, such as about 300 mg to about 500 mg).

More particularly, the single daily dose described above (e.g. at point (i) directly above) may be administered at a time from about 20:00 hours to about 06:00 hours.

In a more particular embodiment, the single daily dose (e.g. described at point (i) above) may be administered at a time from about 21:00 hours to about 05:00 hours (e.g. about 22:00 hours to about 04:00 hours).

In a yet more particular embodiments (particularly wherein the treatment is administered as a pharmaceutical composition that is not formulated for delayed release of the active ingredient), the single daily dose (e.g. described at point (i) above) may be administered at a time from about 02:00 hours to about 06:00 hours (e.g. about 03:00 hours to about 05:00 hours, such as about 04:00 hours).

In further particular embodiments (particularly wherein the treatment is administered as a pharmaceutical composition that is formulated for delayed release of the active ingredient, such as those described in the eight aspect of the invention herein), the single daily dose (e.g. as described at point (i) above) may be administered at a time from about 20:00 hours to about 00:00 hours (e.g. about 21:00 hours to about 23:00 hours, such as at about 22:00 hours).

In alternative embodiments (particularly wherein the treatment is administered as a pharmaceutical composition that is formulated for delayed release of the active ingredient, such as those described in the eight aspect of the invention herein), the single daily dose (e.g. as described at point (i) above) may be administered prior to sleep (i.e. immediately before the patient begins to attempt to sleep, which may alternatively be described as "before bed", "before sleep", or the like).

In particular embodiments of the invention (for example, particular embodiments of the first to seventh aspects of the invention), compounds of the invention may be administered in a manner such that the plasma concentration of valproic acid, or a salt and/or metabolite thereof, during a particular period (e.g. a 24 hour period) mimics the plasma concentration of PAI-1 during the same period.

As used herein, references to a plasma level that "mimics" another will be understood to mean that the relative plasma levels of the two agents follow substantially similar patterns of variation (e.g. the curves obtained by plotting the plasma concentrations of the two agents may be substantially superimposable, although the absolute levels/concentrations of the two agents may be different). The term "mimics" has its ordinary meaning in the art, i.e. to resemble, simulate, approximate, follow or impersonate, but not necessarily replicate exactly or precisely.

The skilled person will understand that, in addition to the evening dose, a lower morning dose may be administered, which dose would be absorbed when the PAI-1 level starts to increase in the late afternoon. For example, in one such treatment 10-500 mg (such as 50-300 mg, more particularly 100 or 200 mg) is administered approximately 10-14 hours (such as e.g. 12 hours) after the evening dose.

Thus, in a particular embodiment of the invention, a lower morning dose is administered, in addition to the evening dose, which dose will consist of about 10 to about 500 mg (such as about 50 to about 300 mg, more particularly about 100 or about 200 mg) that is administered during a time period that is about 10 to about 14 hours (such as e.g. about 12 hours) after the evening dose. In a specific embodiment, this morning dose is about 20 to about 50% (such as about 20, about 30 or about 40%) of the evening dose.

In a more particular embodiment, there is provided a once-daily formulation that provides the same effect as the morning and evening dose described in the embodiment directly above, which may be provided e.g. in the form of a dual layer formulation with a core giving a second small peak coinciding with the rise in PAI-1, or with differently coated and/or formulated granules formulated for such a release profile.

As described herein, it has been found that valproic acid (VPA) potently reduces plasma PAI-1 levels, with such reduction allowing for an increase in the activity of endogenous t-PA. In particular, administration of VPA such that plasma levels thereof coincide with peak plasma levels of PAI-1 allows for the treatment or prevention of pathological conditions associated with excess fibrin deposition and/or thrombus formation.

Thus, references herein (e.g. in the first to seventh aspects of the invention) to uses in treating or preventing a pathological condition associated with excess fibrin deposition and/or thrombus formation may also refer to treating or preventing a pathological condition expected to benefit from (i.e. be treated or prevented by) reduced activity of PAI-1.

For the avoidance of doubt, specific conditions referred to as being associated with excess fibrin deposition and/or thrombus formation, as known to the skilled person (in particular, as described herein), may also be understood to be expected to benefit from (i.e. be treated or prevented by) reduced PAI-1 activity, which may be understood to result from reduced levels of PAI-1 in plasma.

In particular, in a further aspect of the invention, there is provided a method of reducing PAI-1 levels (i.e. levels of PAI-1 in plasma) in a patient in need thereof comprising the step of administering a therapeutically effective amount of valproic acid, or a pharmaceutically acceptable salt thereof.

Similarly, specific methods of treating or preventing conditions associated with excess fibrin deposition and/or thrombus formation as referred to herein may also be understood as being methods of reducing PAI-1 levels in a patient in need thereof.

For example, in a yet further alternative first aspect of the invention, there is provided a method of reducing PAI-1 levels in a patient in need thereof comprising administering at least one dose of a therapeutically effective amount of valproic acid, or a pharmaceutically acceptable salt thereof, to a patient such that the maximum plasma concentration (Cmax) of valproic acid, or a salt and/or metabolite thereof, in the patient occurs during a time period that is from four hours before to one hour after the maximum plasma concentration (Cmax) of PAI-1 in the patient.

As used herein, references to reducing levels of PAI-1 (and, similarly, to reduced (or inhibited) PAI-1 activity, e.g. references to inhibiting PAI-1) may refer to levels of PAI-1 in plasma during treatment with compounds of the invention being at (e.g. reduced to or maintained at) levels lower than (e.g. at least 10% lower than, such as at least 20% lower than, for example at least 30%, at least 40%, at least 50% or at least 60%) levels of PAI-1 occurring prior to treatment with compounds of the invention.

Compounds of the Invention

Again, as indicated herein, the term "compounds of the invention" refers to valproic acid and pharmaceutically acceptable salts thereof, including mixtures thereof. The skilled person will understand that valproic acid may also be referred to as, inter alia, 2-propylpentanoic acid and VPA.

The compounds presented herein include, where relevant, all diastereomeric, enantiomeric, and epimeric forms. For compounds described herein that exist as tautomers, all tautomers are included within the formulas described herein. Further, the compounds described herein may be formed as, and/or used as, salts (e.g. pharmaceutically acceptable salts). The skilled person will understand that references herein to salts of compounds will include references to pharmaceutically acceptable salts.

Compounds described herein may be prepared using techniques and procedures known to those skilled in the art. Exemplary synthetic methods useful for synthesizing the compounds in the application include, for example, those disclosed in Nogrady (1985) Medicinal Chemistry A Biochemical Approach, Oxford University Press, New York, pages 388-392; Silverman (1992); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989).

VPA may be commercially available, for example from Sigma-Aldrich (under product number P4543 as at 1 Oct. 2014). Pharmaceutically acceptable salts of VPA (such as sodium salt thereof) may also be commercially available. It will also be appreciated that VPA, or pharmaceutically acceptable salts thereof, may be synthesised using techniques well known to those skilled in the art.

As described herein, VPA may be formulated and/or administered in the form of a pharmaceutically acceptable salt thereof.

The skilled person will understand that pharmaceutically acceptable salts (e.g. of VPA) may include but are not limited to:
  (a) salts formed when an acidic proton is replaced by a metal ion, such as for example, an alkali metal ion (e.g. lithium, sodium, potassium), an alkaline earth ion (e.g. magnesium, or calcium), or an aluminium ion, or is replaced by an ammonium cation ($NH_4^+$);
  (b) salts formed by reacting VPA with a pharmaceutically acceptable organic base, which includes alkylamines, such as ethanolamine, diethanolamine, triethanolamine, tromethamine, N-methylglucamine, dicyclohexylamine, tris(hydroxymethyl)methylamine, and salts with amino acids such as arginine, lysine, and the like;
  (c) salts formed by reacting VPA with a pharmaceutically acceptable acid, which provides acid addition salts. Pharmaceutically acceptable acids include hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Particular pharmaceutically acceptable salts of VPA that may be mentioned include those mentioned at point (a) above. More particular pharmaceutically acceptable salts of VPA that may be mentioned include those where the carboxylic acid proton is replaced with an alkaline earth ion (e.g. magnesium or calcium) or, more particularly, an alkali metal ion (e.g. lithium, sodium or potassium).

In particular embodiments of each aspect of the invention, VPA is administered and/or formulated (as appropriate) in the form of the sodium salt thereof (i.e. sodium valproate). In more particular embodiments, VPA is administered and/or formulated (as appropriate) in the form of a mixture of VPA (i.e. in the non-salt form) and the sodium salt thereof (i.e. sodium valproate), such as an equal mixture thereof.

For instance, in particular embodiments of the invention (i.e. each aspect of the invention), VPA may administered and/or formulated (as appropriate) in the form of a mixture of the sodium salt thereof (i.e. sodium valproate) and valproic acid. Several such mixtures are known in the art, such as: valproate semisodium, also known as divalproex sodium (1:1 molar relationship between valproic acid and sodium valproate), which is marketed, for example, as Depakote and Depakote ER (by AbbVie Inc.); and valproate sodium (1:2.3 ratio between valproic acid and sodium valproate), which is marketed, for example, as Epilex Chrono.

Additional pharmaceutically acceptable salts that may be mentioned include those described in Berge et al., J. Pharm. Sci. 1977, 66, 1-19; and "Handbook of Pharmaceutical Salts, Properties, and Use", Stah and Wermuth, Ed.; Wiley-VCH and VHCA, Zurich, 2002 (the contents of which are incorporated herein in their entirety).

References to "salts" of compounds of the invention will be understood to refer to salt forms that may occur through exchange of anions or cations with compounds of the invention, for example, in blood plasma. In particular, the term "salts" may also refer to pharmaceutically acceptable salts, such as those described herein.

As described herein, VPA may also be formulated and/or administered in the form of a prodrug thereof, or a pharmaceutically acceptable salt of said prodrug.

As used herein, the term prodrug when used in relation to VPA will be understood to refer a compound that may be converted to VPA in vivo (i.e. following administration).

Such prodrugs may be identified by a person skilled in the art and may include ester (e.g. methyl or ethyl ester) or amide derivatives of VPA. Particular prodrugs that may be mentioned include 2-propylpentanamide (also known as valpromide).

When compounds of the invention are administered in the form of a prodrug thereof, the skilled person will be able to adjust the dose administered in order to achieve the equivalent dose of VPA as required.

Commercially-available products containing valproic acid and/or sodium valproate, or prodrugs thereof, include but are not limited to:

Depakote (AbbVie Inc.), Absenor (Orion Corporation), Convulex (Pfizer), Convulex CR, Depakene/Depakine/Depalept/Deprakine (AbbVie Inc./Sanofi Aventis), Depakine Chrono (Sanofi), Depakene-R (Kyowa Hakko Kogyo), Selenica-R (Kowa), Encorate (Sun Pharmaceuticals India), Encorate Chrono (Sun Pharmaceuticals), Epival (Abbott Laboratories), Epilim (Sanofi), Epilim Chronospheres modified release granules, Epilim Chrono Controlled release tablets, Epilim Chrono Prolonged release tablets, Stavzor (Noven Pharmaceuticals), Valcote (Abbott Laboratories), Valpakine (Sanofi Aventis), Depamide (Sanofi-Avetis), Dipexil-R (Bial), Eliaxim (Bial), Sodium Valproate Sandoz Tablets (Sanofi), Valpro Tablets (Alphapharm), Valproate Winthrop Tablets (Sanofi), Valprease (Sigma), Epilim EC modified release tablets (Sanofi-Aventis), Oriept (Wockhardt), Epilim Chrono (Sanofi) (1:2.3 ratio of valproic acid and sodium valproate), Epilim EC200 (Sanofi), Valprol CR (Intas Pharmaceutical), Episenta prolonged release (Beacon), Valproic Acid capsules, USP (Teva), Stavzor (Noven), Orfiril (Desitin Pharmaceuticals).

Commercially-available products containing valproic acid and/or sodium valproate, or prodrugs thereof, will also include generic version of the above-mentioned formulations, which may be sold/marketed under a different name.

Administration of the Compounds

The skilled person will understand that there is also provided a pharmaceutical composition comprising valproic acid, or a pharmaceutically acceptable salt thereof, and optionally comprising one or more pharmaceutically acceptable excipient, for use in treating or preventing a pathological condition associated with excess fibrin deposition and/or thrombus formation as described in first to seventh aspects of the invention (including all embodiments thereof).

Compounds of the invention may be administered to a subject in a convenient manner such as by the oral, intravenous, intramuscular, subcutaneous, intraperitoneal, intranasal, buccal, transdermal, intradermal, or suppository routes as is known in the art. In particular, compounds of the invention may be administered by the oral route; for example, as a pharmaceutical formulation suitable for oral administration (e.g. a tablet, capsule, buccal film, spray or the like).

In particular, pharmaceutical formulations suitable for oral administration may be presented as discrete units, such as capsules or tablets (e.g. tablets), which each contain a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations.

For example, tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Moreover, formulations for oral use may also be presented as hard gelatine capsules where the active ingredient is mixed with an inert solid diluent, for example, calcium carbonate, lactose, calcium phosphate or kaolin, or a soft gelatine capsules wherein the active ingredient is mixed with water medium (such as a water miscible liquid e.g. poly ethylene glycol) or an oil medium, for example peanut oil, liquid paraffin, or olive oil. Such gelatine capsules may be formulated to contain granules of the active ingredient, which granules may be formulated (e.g. coated) in a manner as described herein for tablets.

Further, formulations for oral use may be presented into the form of tablets composed of compressed microparticles (e.g. granules), which microparticles may be individually coated.

Thus, in embodiments wherein the formulation comprises microparticulates (e.g. in a capsule or tablet, such as a tablet composed of compressed microparticles or capsules containing granules), such microparticles may have different coatings (or formulated for delayed release using polymers as described below), which coatings/formulations may be selected to regulate the release of compounds of the invention; for example, in order to control absorption and render a plasma profile mimicking the PAI-1 plasma profile. The use of such coatings/formulations to control absorption/release of a drug is known in the art and can e.g. be based on different polymers e.g. based on acrylic acid or cellulose and is described more extensively below.

Multiple unit dosage forms are less dependent on the degree of filling of the stomach and may therefore lead to lower variability in e.g. absorption profiles in different patients.

The single compartments of multiple unit dosage forms can be prepared by commonly known methods including granulation, pelletizing, extrusion, hot melt extrusion, tableting and/or coating techniques. For examples on the production of tablets and/or capsules from coated granules/microtablets see e.g. WO 96/01621, WO 96/01624, Siddique, Khanam and Bigoniya, AAPS PharmSciTech 2010. These references also provide information on how different materials can be used to control the release of drug from a tablet or capsule (or from granules in said tablet or capsule).

In particular, the skilled person will be aware that valproic acid is a liquid and sodium valproate is hygroscopic. Suitable excipients and preparation processes for these types of ingredients are known in the art and include e.g. coating of components with a suitable polymer (e.g. methacrylic acid copolymers of different types) and/or water insoluble materials such as waxes/fatty acids etc., in order to achieve reduced hygroscopicity. Such polymers may also be used to delay the release and/or absorption of the drug according to the invention.

For buccal and sublingual use, creams, ointments, jellies, solutions of suspensions and the like containing the compounds of the invention may be employed.

Pharmaceutical compositions may also be in the form of suppositories for rectal administration of the compounds of the invention. These compositions can be prepared by mixing the compounds of the invention with a suitable non-irritating excipient which is solid at ordinary temperatures but liquid at the rectal temperature and will thus melt in the rectum to release the drug. Such materials include, for example, cocoa butter and polyethylene glycols.

Pharmaceutical compositions comprising compounds of the invention may also be provided in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutical forms suitable for injectable use include, but is not limited to, sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of a dispersion, and by the use of surfactants. The preventions of the action of microorganisms can be brought about by various antibacterial and antifungal agents; for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active material in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solution thereof.

We have found that compounds of the invention may be conveniently administered to a subject by the oral route, particularly in the form of a tablet or capsule (e.g. a tablet). Moreover, we have found that the particular dosage regimes contemplated in the invention are particularly suited to oral administration in the form of a tablet or capsule that is formulated such the release of compounds of the invention from said tablet or capsule after oral administration is delayed.

As used herein, references to formulations allowing for delayed or controlled released will be understood by those skilled in the art. In this regard, it will be understood that the terms delayed and controlled may be used interchangeably.

In an eighth aspect of the invention, there is provided a pharmaceutical composition comprising valproic acid, or a pharmaceutically acceptable salt thereof, wherein the composition is in the form of a tablet or capsule for oral administration and is formulated such that substantially all of the valproic acid, or a pharmaceutically acceptable salt thereof, is released during a period from about four to about eight hours after administration.

As used herein, references to a capsule will include capsules filled with the active ingredient in powder form, or in the form of granules and/or microparticles, which granules and/or microparticles may be coated as described herein, and which capsule may itself be coated. Furthermore, the granules may be formulated for specific release profiles using e.g. different delayed/controlled release polymers (and/or coating the granules).

As used herein, references to a tablet will include tablets formed from compressed granules and/or microparticles, which granules and/or microparticles may be coated as described herein, and which tablet may itself be coated.

As used herein (particularly in reference to the eight aspect of the invention, including all embodiments thereof), the term "substantially all" will refer to an amount that is at least 60% of the total amount present (i.e. the total amount included in the composition). In particular, the term may refer to an amount that is at least 70% of the total, such as at least 80% of the total. More particularly, the term may refer to an amount that is at least 90% of the total, such as at least 95% (e.g. at least 99%) of the total.

In a particular embodiment of the eighth aspect of the invention, references to substantially all of the valproic acid, or a pharmaceutically acceptable salt thereof, being released may refer to substantially all of one dose (i.e. at least one therapeutically effective dose) thereof.

The skilled person will understand that the release of the active ingredient may be delayed if the composition is administered with or shortly after food. Thus, references to the time taken for the active ingredient to be released may refer to the time taken for such release when the composition is administered to a patient at least two hours after that patient has consumed food (which may be referred to as administration on an empty stomach, or the like).

It may also be appreciated that it may be beneficial to administer compounds of the invention with food (e.g. to reduce gastrointestinal side-effects). Thus, in a particular embodiment of the first to seventh aspects of the invention, the treatment comprises administering the valproic acid, or a pharmaceutically acceptable salt thereof, with food (e.g. administered to a patient who has consumed food less than two hours prior to administration or who will be directed to consume food within 30 minutes of administration).

As used herein (particularly in reference to the eight aspect of the invention, including all embodiments thereof), references to an active ingredient being "released" (i.e. from a pharmaceutical formulation) will refer to the active ingredient being in a form that is available for absorption (i.e. when administered orally, systemic absorption from the gastro intestinal (GI) tract). When used in relation to tablets and/or capsules for oral administration, the term will indicate that the active ingredient is not contained in said tablet or capsule (which may include the active ingredient being no longer contained within granules (e.g. coated granules) and/or microparticles contained within said tablets or capsules) but is instead distributed in the GI tract.

In a particular embodiment of the eighth aspect of the invention, the pharmaceutical composition is formulated such that substantially all of the valproic acid, or a pharmaceutically acceptable salt thereof, is released during a period from about six to about eight hours after administration (such as about six to about seven hours after administration, or such as about seven to about eight hours after administration, e.g. about seven hours after administration).

In more particular (and alternative) embodiments of the eighth aspect of the invention, the pharmaceutical composition is formulated such that substantially all of the valproic acid, or a pharmaceutically acceptable salt thereof, is released during a period that is:
  (i) from about three to about five hours after administration (from about four to about five hours after administration);
  (ii) from about four to about six hours after administration;
  (iii) from about five to about seven hours after administration;
  (iv) from about six to about eight hours after administration; or
  (v) from about eight to about ten hours after administration.

In a particular embodiment of the eighth aspect of the invention, the pharmaceutical composition may further comprise one or more pharmaceutically acceptable excipient (e.g. a pharmaceutically acceptable adjuvant, diluent or carrier), such as those described herein. In such embodiments, the compounds of the invention may be provided in admixture with said one or more pharmaceutically acceptable excipient.

The skilled person will understand that pharmaceutical formulations (i.e. tablets or capsules) comprising compounds of the invention (such as those described in the eight aspect of the invention, including embodiments thereof) will contain all or part of a therapeutically effective dose of the compounds of the invention.

For the avoidance of doubt, such a dose may be provided in a single unit of the composition (e.g. a single tablet or capsule), or may be provided by the combined administration of several units of the formulation each comprising a corresponding fraction of the dose (e.g. two tablets each containing half of the required dose, or a plurality of microparticles each containing the requisite fraction of the required dose).

In particular, said formulations (e.g. tablets for oral administration) may comprise a single therapeutically effective dose. Thus, in particular embodiments of the eight aspect of the invention, the composition comprises a dose (e.g. a total daily dose) of valproic acid, or a pharmaceutically acceptable salt thereof, as defined in any one or more of the first to seventh aspects of the invention (including all embodiments thereof).

Depending on the dose required, pharmaceutical formulations that may be mentioned include those in which the active ingredient is present in at least 1% (or at least 10%, at least 30% or at least 50%) by weight. That is, the ratio of active ingredient to the other components (e.g. the pharmaceutically acceptable excipient) of the pharmaceutical composition is at least 1:99 (or at least 10:90, at least 30:70 or at least 50:50) by weight.

Thus, the skilled person will understand that the invention further provides a process for the preparation of pharmaceutical formulations as described herein (such as those described in the eight aspect of the invention, including embodiments thereof), which process comprises formulating compounds of the invention in a manner as described herein. In particular, such a process may comprise the steps of:
  (a) bringing compounds of the invention into association with one or more pharmaceutically acceptable excipient (e.g. to form an admixture thereof); and
  (b) formulating as a tablet or capsule (as described herein).

The skilled person will understand that the term bringing into association means that the relevant components are rendered suitable for administration in conjunction with each other.

As described herein, compounds of the invention may be administered and/or formulated in a form coated by, or administered with, a material to delay release of the active ingredient. In particular, formulations in the form of a tablet may be coated with such a material and/or formulated with polymers that regulate the release. Moreover, formulation in the form of a capsule may be formulated such the capsule is composed of, or comprises an amount (i.e. an effective amount) of, such a material.

Thus, pharmaceutical compositions of the eight aspect of the invention may be referred to as "delayed release" or "controlled release" compositions or formulations, or the like.

In such instances, the skilled person will understand that the material to delay release of the active ingredient will be selected and/or formulated in a manner to delay release of the active ingredient for the required time (e.g. for about six hours).

The skilled person will be familiar with materials used to delay (i.e. for delaying) the release of active ingredients, particularly when administered in the form or oral compositions (such as tablets and capsules). Such materials may be described in, for example, Remington's Pharmaceutical Science and U.S. Pharmacopeia (The United States Pharmacopeia-National Formulary (USP-NF)), Remington: The Science and Practice of Pharmacy, 19th Ed. (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, 7th Ed. (Lippincott Williams Wilkins 1999), the contents of which are incorporated herein in their entirety.

For example, materials used to delay the release of active ingredients may include sustained release polymers, such as hydroxypropyl cellulose, hydroxypropyl methylcellulose, carboxymethyl cellulose, chitosan, aloe mucilage, pectin, ethyl cellulose, polyvinyl chloride, polyethylene and polyvinylpyrrolidone (PVP) (e.g. hydroxypropyl cellulose, hydroxypropyl methylcellulose, carboxymethyl cellulose, chitosan, aloe mucilage, pectin, ethyl cellulose, polyvinyl chloride and polyethylene). Moreover, one way of achieving a sustained release coating is to mix a water soluble polymer such as HPMC with a water insoluble polymer such as ethyl cellulose. The skilled person will understand that different materials used and different ratios thereof will result in different release patterns, and will be able to adjust the formulation accordingly (i.e. to achieve the desired release profile).

The skilled person will understand that where compositions are administered and/or formulated in a form coated by, or administered with, a material to delay release of the active ingredient, said material may be composed of more than one pharmaceutically acceptable substance (e.g. one or more pharmaceutically acceptable coating). For example, where compositions of the eight aspect of the invention are administered in the form of a tablet, said tablet may comprise one or more pharmaceutically acceptable coatings of a material to delay release of the active ingredient.

In such instances, the skilled person will understand that the delay of the release of the active ingredient from the composition (e.g. the tablet) is achieved as a combined effect of these coatings. For example, where a tablet is coated so as to delay release for a total of six hours after oral administration, the tablet may comprise two layers of coating, each coating delaying release for three hours (or one coating delaying release for two hours and a further coating delaying release for four hours), i.e. with the first coating being removed to expose the second coating, and so on (in other words, said coatings being exposed in a sequential manner).

In particular embodiments of the eight aspect of invention, where compositions of the eight aspect of invention comprise one or more coatings (e.g. are in the form of a coated tablet), one or more of said coatings may be a coating for preventing release of the active ingredient, or preventing exposure of further coatings, in the stomach. In particular, one or more (e.g. one) of said coatings may be an enteric coating. Said enteric coatings will be well known to the person skilled in the art.

In certain embodiments of the eight aspect of invention (particularly those referring to tablets having one or more coating), the core component (e.g. the core component of a coated tablet) may contain one or more components designed to promote disintegration in aqueous media.

Thus, in a particular embodiment of the eight aspect of the invention, the formulation is provided as a tablet (or capsule) for oral administration comprising one or more coated core (e.g. a single coated core, or a plurality of coated granules or microparticles each having such a core), said core(s) containing valproic acid or a pharmaceutically acceptable salt thereof, wherein:
  (i) said coating is formed of material selected and/or formulated in a manner to delay release of the active ingredient for the required time (e.g. for about six hours); and (ii) said core is formulated to in a manner designed promote disintegration in aqueous media (e.g. comprising one or more disintegrants).

Such disintegrants will be well known to those skilled in the art, including agents designed to swell upon contact with aqueous media.

The skilled person will understand that there are several materials that can be used to form an enteric coating on a tablet/capsule and/or granules/microtablets/pellets/multiparticulate/multiple unit dosage forms. These include but are not limited to shellac, waxes, fatty acids, polymers, plastics and plant fibers.

Examples of such polymers include, but are not limited to, hypromellose phthalate (hydroxypropyl methylcellulose phthalate, HPMCP), hypromellose acetate succinate, cellulose acetate trimellitate, acrylic acid/methacrylic acid copolymers (e.g. poly(methacrylic acid-co-methyl methacrylate), cellulose acetate phthalate (CAT), poly(vinyl acetate phthalate, PVAP) and ethyl acrylate. Other materials for enteric coating include dextrins, amylose starch and starch derivatives, sodium alginate, Zein and Aqua-Zein R.

Commercially available systems for enteric coatings and coatings for sustained release include variants of OPADRY® (Colorcon), Titancoat, Kollicoat® (BASF), Eudragit®, (e.g. Eudragit® RL, Eudragit® RS, Eudragit® S, Eudragit® L and Eudragit® E), Sheffcoat EC and Sheffcoat Ent.

The skilled person will understand that different materials have different properties e.g. when it comes to the dissolution pH and can thus be used to control the absorption pattern, e.g. delaying release of a drug for a specific time, by a person skilled in the art. In addition, the thickness of the coating can also be altered to achieve a specific pattern. Furthermore, if coated granules are used e.g. in a capsule or compressed tablet, different coatings (and/or coating thicknesses) can be used in order to mimic the pattern of PAI-1 plasma concentration for the compounds of the invention. More specifically, a combination of several (e.g. 2-5) differently coated granules/microparticles may be used to achieve the desired effect in mimicing the pattern of PAI-1 plasma concentration for the compounds of the invention.

One way of extending the delay in absorption of an enteric coating is to mix an enteric coating polymer with a smaller amount of a sustained release polymer; as described in e.g Tirpude and Puranik, J Adv Pharm Technol Res 2011, where 10% of sustained release acrylic polymers (Eudragit NE30D) was mixed with 90% enteric acrylic polymers (Eudragit L30D555). Thus, materials such as polymers with different dissolution characteristics may be combined in different ratios to achieve a desired pattern of absorption according to the invention. Other examples of methods to achieve different absorption patterns by using various grades of hydrophilic polymers and how to make matrix tablets from granules are described in Roy, Brahma, Nandi and Parida, Int J Appl Basic Med Res. 2013.

Different ways to achieve controlled release using matrix tablets and description of different polymers and matrices is also described in http://www.pharmainfo.net/reviews/matrix-tablets-important-tool-oral-controlled-release-dosage-forms, the disclosures of which are incorporated herein by reference in their entirety.

For more details on enteric coatings see e.g. Singh Deep Hussan et al., IOSR Jounal of Pharmacy (2012), and the Handbook of Pharmaceutical Excipients Rowe, Raymond C; Sheskey, Paul J; Cook, Walter G; Fenton, Marian E., Seventh edition, the disclosures of which are incorporated herein by reference in their entirety.

Some coatings may require the use of plasticizer/s to obtain good results and the use of such agents is known in the art. Such plasticizers include e.g. citrate esters, glycerol, propylene glycol, diethyl phthalate, dibutyl phthalate, dibutyl sebacate, tributul citrate, acetylated monoglycerides, triacetin and glycerintriacetate.

Pigments and/or these plasticizers may be added to e.g. a polymeric solution in order to improve the technical properties of e.g. a membrane or modify the release characteristics.

Compounds of the invention may be coated by, or administered with, a material to prevent their inactivation. For example, the active material may be administered in an adjuvant, co-administered with e.g. enzyme inhibitors or in liposomes. Adjuvants contemplated herein include, but are not limited to, resorcinols, non-ionic surfactants such as polyoxyethylene oleyl ether and n-hexadecyl polyethylene ether. Enzyme inhibitors include; but are not limited to, pancreatic trypsin inhibitor, diisopropylfluorophosphate (DFP) and trasylol. Liposymes include water-in-oil-in-water P40 emulsions as well as conventional liposomes. Dispersions can also be prepared in glycerol, liquid polyethylene glycols, and mixtures thereof and in oils. Under ordinary conditions of storage and use, these preparations contain a preservative to prevent the growth of microorganisms.

As described herein, the skilled person will understand that when administered orally the active compound may be combined with an inert diluent or with an edible carrier, or it may be enclosed in hard or soft shell gelatin capsule, or it may be compressed into tablets, or it may be incorporated directly with the food of the diet. For oral therapeutic administration, the active material may be incorporated with excipients and used in the form of ingestible tablets, buccal tablets, troches, capsules, elixirs, suspensions, syrups, wafers, and the like. In addition, the active material may be incorporated into sustained-release preparations and formulations. For example, the active material may be incorporated in enterotablets/capsules and/or bi-phasic release formulations, which formulations will be known to the skilled person. For example, bi-phasic release formulation may be of the type described in US2007/0232528A1 (the contents of which are incorporated herein in their entirety), which formulations may be suitable for administration during a period from about 22:00 to 00:00 hours (e.g. about 23:00 hours).

As used herein, the term "pharmaceutically acceptable excipient" will include pharmaceutically acceptable adjuvants, diluents and carriers, as known to those skilled in the art. This may include any and all solvents, dispersion media, coatings, antibacterial and antifungal agents, isotonic and absorption delaying agents and the like.

Thus, the tablets, troches, pills, capsules, and the like may also contain the following: a binder such as gum tragacanth, acacia, corn starch, or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially non-toxic in the amounts employed.

The use of such excipients is well known in the art; see, for example, Remington's Pharmaceutical Science and U.S. Pharmacopeia (The United States Pharmacopeia-National Formulary (USP-NF)), Remington: The Science and Practice of Pharmacy, 19th Ed. (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, 7th Ed. (Lippincott Williams Wilkins 1999).

As described herein, tablets and/or capsules formulated to delay the release of compounds of the invention from said tablet after oral administration (as described in the eight aspect of the invention, and embodiments thereof) are particularly suited for use in treating or preventing a pathological condition associated with excess fibrin deposition and/or thrombus formation in accordance with the particular dosage regimes described herein.

Thus, in a ninth aspect of the invention, there is provided a pharmaceutical composition as described in the eight aspect of the invention (including any one or more embodiments thereof) for use in treating or preventing a pathological condition associated with excess fibrin deposition and/or thrombus formation, wherein said treatment is as described in any one of the first to seventh aspects of the invention (including any one or more embodiments thereof).

In an alternative ninth aspect of the invention, there is provided the use of a pharmaceutical composition as described in the eight aspect of the invention (including any one or more embodiments thereof) in the manufacture of a medicament for use in treating or preventing a pathological condition associated with excess fibrin deposition and/or thrombus formation, wherein said treatment is as described in any one of the first to seventh aspects of the invention (including any one or more embodiments thereof).

In a further alternative ninth aspect of the invention, there is provided a method of treating or preventing a pathological condition associated with excess fibrin deposition and/or thrombus formation in a patient in need thereof as described in any one of the first to seventh aspects of the invention (including any one or more embodiments thereof), wherein the valproic acid or pharmaceutically acceptable salt thereof is administered in the form of a pharmaceutical composition as described in the eight aspect of the invention (including any one or more embodiments thereof).

As described herein, the skilled person will be able to adjust the formulation and manner of administration of compounds of the invention in order to achieve the desired parameters, such as the desired timing and/or levels of plasma concentrations of specific agents.

For instance, the skilled person will be aware that various formulations of compounds of the invention are commercially available and may be administered in a manner suitable for use in, inter alia, treatments as described in the first to seventh aspects of the invention.

Thus, in particular embodiments of invention (for example, particular embodiments of the first to seventh and ninth aspects of the invention) there is provided valproic acid, or a pharmaceutically acceptable salt thereof, for use in treating or preventing a pathological condition associated with excess fibrin deposition and/or thrombus formation, wherein said treatment comprises administering a pharmaceutical composition comprising a dose of valproic acid, or a pharmaceutically acceptable salt thereof, to a patient in a form (i.e. a specific formulation), and at a specific dose and time, as indicated in the following table.

| Formulation name | Dose of active agent | Time of administration |
|---|---|---|
| Depakote | 125 to 750 mg (e.g. 250 mg or 500 mg) once daily | Approximately 22:00 hours to 00:00 hours (e.g. about 23:00), or before sleep. If administered with food absorption may be delayed and the drug can be administered from approximately 19:00 to 21:00 hours. |
| Depakote ER | 250 to 750 mg (e.g. 250 or 500 mg) once daily | Approximately 18:00 to 21:00 (e.g. about 19:00), or before sleep. |
| Depakote sprinkle capsules | 125 to 750 mg (e.g. 250 or 500 mg) once daily | Approximately 22:00 hours to 00:00 hours (e.g. about 23:00), or before sleep. If administered with food absorption may be delayed and the drug can be administered from approximately 20:30 to 23:00 hours (e.g. about 22:00). |
| Orfiril enterotablets | 150 to 750 mg (e.g. 300 mg or 600 mg) once daily | 22:00 hours to 00:00 (e.g. about 23.00) or before sleep. |
| Orfiril Long depot granules | 200 to 600 mg (e.g. 500 mg) once daily | 20:00 hours to 00:00 (e.g. about 22:00) or before sleep. |
| Ergenyl enterotablets | 200 to 600 mg (e.g. 300 mg or 500 mg) once daily | 21:00 hours to 00:00 (e.g. about 23:00) or before sleep. |
| Ergenyl Retard depot granules | 100 to 750 mg (e.g. 250 mg or 500 mg) once daily | 22:00 to 01:00 (e.g. about 23:00) or before sleep. |
| Absenor enterotablets | 100-600 (e.g. 300 or 500 mg) once daily | 21:00 to 00:00 (e.g. about 23.00) or before sleep. If administered with food absorption may be delayed and the drug can be administered from approximately 19:00 to 22:00 hours. |
| Absenor tablets | 300 to 600 mg (e.g. 300 mg) once daily | 23:00 to 01:00 (e.g. about 00.30) or before sleep. |
| Convulex capsules | 150 to 600 mg (e.g. 300 or 500 mg) once daily | 21:00 hours to 00:00 (e.g. about 23:00) or before sleep. |
| Epilim gastroresistant tablets | 100 to 600 mg (e.g. 400 or 500 mg) once daily | 21:00 to 00:00 (e.g. about 23.00) or before sleep. |
| Epilim Chrono/ Depakine Chrono | 200 to 800 mg (e.g. 300 or 500 mg) once daily | 20:00 to 00:00 (e.g. about 22.00) or before sleep. |
| Epilim Chronospheres | 100 to 750 (e.g. 250 or 500 mg) once daily | 19:00 to 22:00 (e.g. about 20:30) or before sleep. |
| Valprotek CR | 300 to 600 mg (e.g. 300 or 500 mg) once daily | 19:00 to 22:00 (e.g. about 20.30) or before sleep. |
| Depakene capsules | 250 to 750 mg (e.g. 250 or 500 mg) once daily | 21:00 hours to 00:00 (e.g. about 23:00) or before sleep. |
| Depakene R | 200 to 600 mg (e.g. 400 mg) once daily | 16:00 to 19:00 (e.g. about 17:30) |
| Selenica R | 200 to 600 mg (e.g. 400 mg) once daily | 9:00 to 12:00 (e.g. about 10:30) |
| Episenta Prolonged release capsules | 150 to 750 mg (e.g 300 or 600 mg) once daily. | 21:00 hours to 00:00 (e.g. about 22:00) or before sleep. |
| Episenta Prolonged release granules | 150 to 750 mg (e.g 300 or 600 mg) once daily. | 21:00 hours to 00:00 (e.g. about 22:00) or before sleep. |

-continued

| Formulation name | Dose of active agent | Time of administration |
|---|---|---|
| Stavzor delayed release capsules | 150 to 750 mg (e.g 300 or 600 mg) once daily. | 23:00 hours to 01:00 (e.g. about 23:30) or before sleep. If administered with food absorption may be delayed and the drug can be administered from approximately 20:00 to 23:00 hours. |
| Valproic Acid capsules, USP (Teva) | 250 to 750 mg (e.g. 250 mg or 500 mg) once daily | Approximately 22:00 hours to 00:00 hours (e.g. about 23:00), or before sleep. If administered with food absorption may be delayed and the drug can be administered from approximately 19:00 to 21:00 hours. |

As used herein, references to the name of certain formulations will refer to the corresponding formulation as sold/marketed in the relevant territory (e.g. in the US, UK or Sweden) as on 1 Oct. 2014.

References in the above table to specific formulations by a specific name will include references to substantially identical formulations that may be referred to by another name (e.g. identical formulations sold and/or marketed using a different product name).

As described herein, the skilled person will understand that administration of a formulation to a patient with or shortly after food may delay release of the active ingredient and will be able to adjust the time of administration accordingly. Unless otherwise stated, references herein to administration of a particular formulation at a particular time (e.g. within a particular time period) will refer to administration to the patient on an empty stomach.

Combination Treatments

Compounds of the invention may also be administered in combination with (e.g in a combined formulation with) other therapeutic agents that are useful in the treating or preventing a pathological condition associated with excess fibrin deposition and/or thrombus formation.

In particular, pharmaceutical compositions as described in the eight aspect of the invention (including embodiments thereof) may comprise compounds of the invention together with one or more pharmaceutically acceptable excipients and one or more other therapeutic agents that are useful in the treating or preventing a pathological condition associated with excess fibrin deposition and/or thrombus formation.

In a particular embodiment of the first to seventh aspects of the invention, the valproic acid or pharmaceutically acceptable salt thereof is administered in combination with one or more (e.g. one) other therapeutic agents that are useful in the treating or preventing a pathological condition associated with excess fibrin deposition and/or thrombus formation.

In a particular embodiment of the eight aspect of the invention, the pharmaceutical formulation further comprises one or more (e.g. one) other therapeutic agents that are useful in the treating or preventing a pathological condition associated with excess fibrin deposition and/or thrombus formation. In such embodiments, the compounds of the invention may be provided in admixture with said one or more other therapeutic agent.

Thus, the skilled person will understand that the invention further provides a process for the preparation of pharmaceutical formulations as described herein (such as those described in the eight aspect of the invention, including embodiments thereof), which process comprises the steps of:

(a) bringing compounds of the invention into association with one or more pharmaceutically acceptable excipient (e.g. to form an admixture thereof) and/or one or more (e.g. one) other therapeutic agents that are useful in the treating or preventing a pathological condition associated with excess fibrin deposition and/or thrombus formation; and (b) formulating as a tablet or capsule (as described herein, e.g. with one or more coating).

As referred to herein, other therapeutic agents that are useful in the treating or preventing a pathological condition associated with excess fibrin deposition and/or thrombus formation include: one or more anti-thrombolytic agents; and/or one or more anticoagulant agents; and/or one or more antiplatelet agents; and/or one or more vasodilators, as known to those skilled in the art.

In particular embodiments, compounds of the invention may administered and/or formulated in combination with:
  one or more anti-platelet agents, including but not limited to aspirin, persantin, ticagrelor and clopidogrel;
  one or more anticoagulant agents, such as heparin, low molecular weight heparin (LMWH), warfarin, anisindione, phenindone, bishydroxycoumarin, bivalirudin, eptifibatid; one or more vasodilators such as nitriles (for example, amylnitrile, nitroglycerin, sodium nitrile, isosorbide dinitrate), papaverine, nicotinic acid and cyclandelate.
  one or more agents preventing cardiovascular events such as, but not limited to statins, beta blockers, angiotensin converting enzyme inhibitors, angiotensin II receptor antagonists or diuretics; and/or
  one or more anti-inflammatory agents including steroids and NSAIDs (including but not limited to aspirin, ibuprofen, naproxen and diclofenac);
  one or more thrombolytic agents selected from, for example, recombinant t-PA, prourokinase, urokinase or streptokinase.

In more particular embodiments, compounds of the invention may be administered and/or formulated in combination with aspirin (i.e. a therapeutically effective amount of aspirin).

In yet more particular embodiments, compounds of the invention may be administered and/or formulated in combination with clopidogrel (i.e. a therapeutically effective amount of Clopidogrel) or ticagrelor (i.e. a therapeutically effective amount of ticagrelor).

For the avoidance of doubt, the skilled person will understand that the term "administered in combination with" includes concomitant, sequential and separate administration. In this regard, sequential administration may refer to administration within the same therapeutic intervention (e.g. within one hour of the compound of the invention).

The skilled person will understand that references to an agent being administered in combination with another agent may also include a kit-of-parts comprising the relevant agents (i.e. as separate components within the same kit).

The skilled person will also understand that references to a first agent being administered in combination with a second agent will also the second agent being administered in combination the first agent, and so forth.

Patient Groups

The skilled person will understand that references herein to a "patient" will refer to living animals who may be subject to the treatment or prevention described herein. In particular, the term patient will refer to a mammal. More particularly, the term patient will refer to a human (such an adult human).

Compounds of the invention may be particularly useful in the treatment or prevention of (particularly, the prevention of) a pathological condition associated with excess fibrin deposition and/or thrombus formation (such as those described herein) in patients at increased risk of developing one or more such condition.

In a particular embodiment of the first to seventh aspects of the invention (including all embodiments thereof), the treatment or prevention (e.g. the prevention, which may also be referred to as prophylaxsis) is in a patient at increased risk of developing a pathological condition associated with excess fibrin deposition and/or thrombus formation (which the skilled person will understand as referring to reducing the risk of the relevant condition, as described herein).

As described herein, several conditions and risk factors are associated with increased susceptibility to thrombotic events (i.e. thrombus formation). These include atherosclerosis, hypertension, abdominal obesity, smoking, sedentary lifestyle, and low-grade inflammation. Thus, in particular embodiments of the first to seventh aspects of the invention (including all embodiments thereof), the treatment or prevention (e.g. the prevention, which may also be referred to as prophylaxsis) is in a patient having one or more such condition/risk factor.

In more particular embodiments, the patient at increased risk of developing a pathological condition associated with excess fibrin deposition and/or thrombus formation is a patient who:
(i) is suffering from one or more medical condition associated with increased risk of thrombus formation, such as metabolic syndrome (e.g. type II diabetes), oncologic diseases, heart failure, renal failure and/or sepsis;
(ii) has previously experienced one or more incidence of a pathological condition associated with excess fibrin deposition and/or thrombus formation, such as one or more incidence of myocardial infarction, ischemic stroke and pulmonary embolism (e.g. one or more incidence of ischemic stroke, such as a major ischemic stroke, minor ischemic stroke or TIA); and/or
(iii) has one or more lifestyle and/or environmental factors placing them at said increased risk, such the patient being a smoker, obese and/or having decreased mobility (e.g. the patient is bed-ridden, such as a patient in a medical unit or elderly care unit).

Thus, in particular embodiments, references to a patient at increased risk of developing a pathological condition associated with excess fibrin deposition and/or thrombus formation will include references to an obese patient, e.g. a patient with a body mass index (BMI) that is above 25 (e.g. above 30 and above 35).

As used herein, references to a patient at increased risk of developing a pathological condition associated with excess fibrin deposition and/or thrombus formation may also include patients (e.g. human male patients) who are 50 years of age or older (e.g. 60 years of age or older).

In particular embodiments, a patient at increased risk of developing a pathological condition associated with excess fibrin deposition and/or thrombus formation may also be a patient who has elevated PAI-1 levels.

For example, as described herein, a patient at increased risk of developing a pathological condition associated with excess fibrin deposition and/or thrombus formation may also be a patient who is suffering from local or systemic inflammation, such as that associated with elevated PAI-1 levels.

Thus, in particular embodiments, a patient at increased risk of developing a pathological condition associated with excess fibrin deposition and/or thrombus formation may be a patient having PAI-1 levels in morning plasma above about 20 ng/ml (e.g. above about 40 ng/ml, such as above about 60 ng/ml, e.g. above about 80 ng/ml or, more particularly, above about 100 ng/ml).

For example, a patient at increased risk of developing a pathological condition associated with excess fibrin deposition and/or thrombus formation may be a patient having PAI-1 levels in morning plasma above about 20 ng/ml (e.g. above about 40 ng/ml, such as above about 60 ng/ml, e.g. above about 80 ng/ml or, more particularly, above about 100 ng/ml) and having experienced one or more incidence of myocardial infarction, ischemic stroke and pulmonary embolism (e.g. one or more incidence of ischemic stroke, such as a major ischemic stroke, minor ischemic stroke or TIA).

In certain embodiments, the patient is not suffering from a:
(i) a CNS or psychiatric disorder, such as epilepsy, migraine and/or bipolar disorder; and/or
(ii) Fragile X syndrome and/or familial adenomatous polyposis.

Thus, in a particular embodiment of the first to seventh aspects of the invention (including all embodiments thereof), the treatment or prevention (e.g. the prevention) is in a patient who is:
(a) at increased risk of developing a pathological condition associated with excess fibrin deposition and/or thrombus formation (particularly as defined herein); and
(b) is not suffering from a CNS or psychiatric disorder (as defined herein, particularly epilepsy and/or bipolar disorder).

FIGURES

FIG. 1 shows a schematic representation of the circadian rhythm (i.e. variation) of PAI-1 levels in an adult human during a typical 24 hour period. The lower curve represents the variation of PAI-1 levels in a normal (i.e. healthy) patient. The upper curve represents the variation in PAI-1 levels in a patient having increased levels of PAI-1 (e.g. patients with obesity and/or the metabolic syndrome). The y-axis represents arbitrary plasma levels and is abbreviated to illustrate the positively skewed distribution toward high plasma levels in obesity/metabolic syndrome. The x-axis represents clock time.

EXAMPLES

The following examples are included to further illustrate the invention, although the skilled person will understand that the invention is in no way restricted to the specific aspects described therein.

Example 1—VPA and PAI-1

The effects of VPA on PAI-1 were analysed in two different proof-of-concept studies in healthy subjects as well as in patients with manifest atherosclerotic disease. The studies had a randomized cross-over design and PAI-1 levels were investigated before and after HDAC inhibition with valproic acid. PAI-1 plasma levels were measured in the morning at the first day of the study as well as at the end of the treatment period with VPA (see example 2 for details on the PAI-1 analysis).

In the first study, 10 healthy non-smoking white male subjects (with mean BMI of approximately 26), aged 50-70 years were included and treated with valproic acid 500 mg (Ergenyl Retard, Sanofi) twice daily during 14 days. Unexpectedly we detected a more than 50% reduction (from 22.2 to 10.8 ng/ml, p<0.05) in circulating plasma PAI-1 levels during mid-morning in comparison to the midmorning levels found before treatment with VPA.

In the second study, 16 non-smoking white male patients, aged 50-80 years with a history of a myocardial infarction were included. On top of their ordinary prescription (beta-blocker, ACE-inhibitor, statin, aspirin) they were treated with valproic acid 500 mg (Ergenyl Retard, Sanofi), twice daily during 28 days. In this study we detected a 45% reduction in circulating plasma PAI-1 levels (from 19.6 ng/ml to 11 ng/ml (p=0.01)), during midmorning.

Example 2—Intermediate Endpoint Study: Effects of Valproic Acid on In Vivo PAI-1 in Man An intermediate endpoint proof-of-concept study is performed in patients with TIA/minor stroke investigated before and after treatment with Valproic acid. Valproic acid is administrated as an enteric-coated tablet with delayed absorption.

The study comprises 20 patients with TIA/minor stroke. Patients are investigated before and after oral treatment with 400 mg valproic acid once time daily at 11 pm for 2 weeks. Plasma PAI-1 levels and plasma concentrations of valproic acid is followed daily during the study period at the following time-points: 3 am, 6 am, 10 am, 16 pm, 22 pm PAI-1 levels are measured by commercially available ELISA-kits (Coaliza PAI-1, Chromogenix AB) and the plasma concentration of valproic acid an metabolites thereof is analyzed according to clinical routine at the Sahlgrenska University laboratory, Gothenburg, Sweden.

The plasma concentration of valproic acid is found to peak between 3 am and 6 am and thereafter declines to very low levels during the trough in PAI-1 concentrations. The peak in plasma valproic acid coincides with the peak level of plasma PAI-1 between 3 am and 6 am. The plasma concentration of valproic acid and plasma PAI-1 levels follow each other with a pronounced circadian elevation with its peak during the early morning hours. The plasma PAI-1 levels are lowered by approximately 30% after the treatment.

Example 3—Clinical Outcome Study in High-Risk Patients for Prevention of Recurrent Thromboembolic Events Using Valproic Acid A clinical outcome study is performed in high-risk patients who have experienced a recent major atherothrombotic cardiovascular event (myocardial infarction or TIA/ischemic stroke) to investigate the preventive effect of valproic acid treatment on the risk for recurrent events. The annual risk for a recurrent atherothrombotic event in the investigated population is estimated to approximately 7%.

Patients are randomized in a parallel study design to receive double-blind oral treatment with 400 mg valproic acid (as in Example 2) or placebo once time daily at 11 pm, in addition to optimal conventional treatment. The event rate is monitored by Kaplan-Meyer statistics. The primary efficacy endpoint is the composite measure of either mortality, or non-fatal myocardial infarction or ischemic stroke. The study is event-driven to a total of 180 events.

The study is expected to show that long-term valproic acid treatment reduces this risk by approximately 30% in addition to that of conventional therapy, i.e. lowers the annual absolute event rate to approximately 5%. Thus, the study is expected to confirm the clinical efficacy and feasibility of using valproic acid for secondary prevention of cardiovascular disease.

The invention claimed is:

1. A method of reducing plasminogen activator inhibitor 1 (PAI-1) plasma levels in a subject in need thereof, comprising administering to the subject a therapeutically effective amount of valproic acid, or a pharmaceutically acceptable salt thereof, thereby reducing PAI-1 plasma levels in the subject.

2. The method of claim 1, wherein the subject has elevated plasma PAI-1 levels relative to the general population.

3. The method of claim 2, wherein the subject has morning plasma levels of PAI-1 greater than 20 ng/ml.

4. The method of claim 1, wherein the subject is a human.

5. The method of claim 1, wherein the valproic acid or a pharmaceutically acceptable salt thereof is administered as a single daily dose.

6. The method of claim 1, comprising administering to the subject at least one dose of a therapeutically effective amount of valproic acid, or a pharmaceutically acceptable salt thereof, wherein the maximum plasma concentration (Cmax) of the valproic acid, or salt and/or metabolite thereof in the subject after administration occurs during a time period that is from four hours before to one hour after the Cmax of PAI-1 in the subject.

7. The method of claim 6, wherein the at least one dose is administered during a time period from about 8 pm to about 6 am.

8. The method of claim 7, wherein the time period is from about 2 am to about 6 am.

9. The method of claim 6, wherein the at least one dose of valproic acid, or the pharmaceutically acceptable salt thereof, is from about 50 to about 1000 mg.

10. The method of claim 6, wherein the at least one dose of valproic acid, or the pharmaceutically acceptable salt thereof, is from about 200 mg to about 600 mg.

11. The method of claim 6, wherein the at least one dose is a single dose.

12. The method of claim 6, wherein the valproic acid, or a pharmaceutically acceptable salt thereof, is in the form of a tablet or capsule for oral administration and at least 60% of the valproic acid, or the pharmaceutically acceptable salt thereof, is released from the tablet or capsule during a time period from about four to about eight hours after administration, or during a time period from about 2 am to about 6 am.

13. The method of claim 6, wherein the valproic acid, or a pharmaceutically acceptable salt thereof, is in the form of a tablet or capsule for oral administration and at least 70% of the valproic acid, or the pharmaceutically acceptable salt thereof, is released from the tablet or capsule during a time period from about four to about eight hours after administration, or during a time period from about 2 am to about 6 am.

14. The method of claim 6, wherein a second dose is administered, and the second dose comprises about 10 mg to about 500 mg of valproic acid, or a pharmaceutically acceptable salt thereof, which is administered about 10 hours to about 14 hours after the at least one dose.

15. The method of claim 1, wherein the valproic acid or a pharmaceutically acceptable salt thereof is administered at a dose sufficient to achieve a reduction in PAI-1 plasma levels of at least about 20%.

16. The method of claim 15, wherein PAI-1 plasma levels are reduced below 20 ng/ml.

17. The method of claim 15, wherein the valproic acid, or a pharmaceutically acceptable salt thereof, is in the form of a tablet or capsule for oral administration, and substantially all of the valproic acid, or a pharmaceutically acceptable salt thereof, is released from the tablet or capsule during a time period from about 2 am to about 6 am.

* * * * *

UNITED STATES PATENT AND TRADEMARK OFFICE
CERTIFICATE OF CORRECTION

PATENT NO. : 12,245,999 B2
APPLICATION NO. : 17/816486
DATED : March 11, 2025
INVENTOR(S) : Jern et al.

Page 1 of 1

It is certified that error appears in the above-identified patent and that said Letters Patent is hereby corrected as shown below:

On the Title Page

(56) References Cited, OTHER PUBLICATIONS, Page 2, Column 2, Tabrizi, et al. cite, Line 61: Please correct "(IPA)" to read --(tPA)--

In the Specification

Column 11, Line 13: Please correct "PAH" to read --PAI-1--

Column 17, Line 24: Please correct "2.0 m/I" to read --2.0 m/l--

Signed and Sealed this
Fifth Day of August, 2025

Coke Morgan Stewart
*Acting Director of the United States Patent and Trademark Office*